(12) United States Patent
Tan et al.

(10) Patent No.: US 6,287,855 B1
(45) Date of Patent: *Sep. 11, 2001

(54) NUCLEIC ACID ENCODING RAT GALANIN RECEPTOR (GALR2)

(75) Inventors: Carina Tan, Metuchen; Kathleen Sullivan, Springfield, both of NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/993,088

(22) Filed: Dec. 18, 1997

Related U.S. Application Data

(60) Provisional application No. 60/033,851, filed on Dec. 27, 1996.

(51) Int. Cl.$^7$ .............................. C12N 15/11; C12N 5/10; C12N 15/12; C12N 15/63
(52) U.S. Cl. .................. 435/320.1; 536/23.5; 435/325
(58) Field of Search ................... 536/23.5; 435/320.1, 435/325, 69.1; 530/350

(56) References Cited

U.S. PATENT DOCUMENTS 5,972,624    10/1999    Smith et al. ..................... 435/7.2

FOREIGN PATENT DOCUMENTS

WO 97/26853    7/1997    (WO).
WO 97/46681    12/1997    (WO).
WO 98/03548    1/1998    (WO).

OTHER PUBLICATIONS

Reeck et al. (Aug. 1987) Cell 50:667.*

George et al. (1988) Macromolecular Sequencing and Synthesis: Selected Methods and Applications (Ed. by D.H. Schlesinger) Alan R Liss, Inc., New York, pp. 127–149.*

Habert–Ortoli, et al. 1994. Proc. Nat. Acad. Sci., USA 91:9780–9783 Molecular cloning of a functional human galanin receptor.

O'Dowd, B. F. et al. 1995 Genomics 28:84–91. The Cloning and Chromosomal Mapping of Two Novel Human Opioid–Somatostatin–like Receptor Genes, GPR7 and GPR8, Expressed in Discrete Areas of the Brain.

Suke Wang, et al., Federation of European Biochemical Societies Letters, 411 (1997) 225–230; Genomic organization and functional characterization of the mouse GalR1 galanin receptor.

IASP Press (Seattle) Abstracts 8th World Congress on Pain (International Assoc. for the Study of Pain) Aug. 19, 1996, ISBN: 0–931092–17–5, Lib. of Congress 96–77433.

* cited by examiner

*Primary Examiner*—Michael Pak
(74) *Attorney, Agent, or Firm*—Sheldon O. Heber; Jack L. Tribble

(57) ABSTRACT

A new galanin receptor, GALR2, is described. Also provided are nucleic acids encoding same and various assays to identify ligands particular to said receptor. Ligands so identified are useful for the treatment of obesity, treatment of pain, and treatment of cognitive disorders.

6 Claims, 26 Drawing Sheets

```
         10         20         30         40
CGCTCCCTCC ACACCTCCAG GGGCAGTGAG CCACTCAAGT  40
CTAAAGCAGA GCGAGTCCCA GGACTTGAGC GCGGGAAGCG  80
AATGGAGTCA GGGTCATTCG ATTGCACCTC TCTCGGCTGC 120
GGGCCGGAGC GGGGTACCAT CCTACACTCT GGGTGCTCCC 160
TCCTCCTCCC GTCCCCGCG CACCCCTGCC CTGGCTCCTG 200
        210        220        230        240
GAGCTCGGCA GTCTCGCTGG GGCGCTGCAG CGAGGGAGCA 240
GCGTGCTCAC CAAGACCCGG ACAGCTGCGG GAGCGGCGTC 280
CACTTGGTG ATACCATGAA TGGCTCCGGC AGCCAGGGCG 320
CGGAGAACAC GAGCCAGGAA GGCGGTAGCG GCGGCTGGCA 360
GCCTGAGGCG GTCCTTGTAC CCCTATTTTT CGCGCTCATC 400
        410        420        430        440
TTCCTCGTGG GCACCGTGGG CAACGCGCTG GTGCTGGCGG 440
TGCTGCTGCG CGGCGGCCAG GCGGTCAGCA CCACCAACCT 480
GTTCATCCTC AACCTGGGCG TGGCCGACCT GTGTTTCATC 520
CTGTGCTGCG TGCCTTTCCA GGCCACCATC TACACCCTGG 560
ACGACTGGGT GTTCGGCTCG CTGCTCTGCA AGGCTGTTCA 600
        610        620        630        640
TTTCCTCATC TTTCTCACTA TGCACGCCAG CAGCTTCACG 640
CTGGCCGCCG TCTCCCTGGA CAGGTAAAGG ACCCAGAAAG 680
AAACATCCAG TATGCCCGGA GGGATCTTGA CTGGAAAAGA 720
CTGAATCCTG GTCTGGTGAC CTTAGTTCCC TGCCCTTTCA 760
CATCACTTGG ACATTCCCAC AGAAGAGCGG TGAAGAGGCG 800
        810        820        830        840
GTGGTCCTTA TTCTCCTCTG GTTTCCACTG AGTGCAACAT 840
GTGCGTCCTG AGTACGCTGG AGGGACTCAC AAAATTTCAG 880
CTTTCTTTAG GAGTTTCCTT GCTGTAGTTT GACCCAAGTC 920
TTCTCCAGGT TTCTGTCAGA ACCTCAGGCA TGAGGGATCT 960
GCCTCCCCTG GTTGTCACCA GAGGATAACA ATCACTGCCC 1000
       1010       1020       1030       1040
CCAGAAATCC AGACAGATTC TACAACTTTT AGTCTTCGGT 1040
GTTTGGGGG TGCCCCTTCA CGTGGAGTAG GTCGGTGGCC 1080
ACATTCCCAG GAGTGACAAT AGCCTAGCAG TGAATCCTCT 1120
CGCTTAGCTG ATGCCCCCC ACTGTCCCCA CAGGTATCTG 1160
GCCATCCGCT ACCGCTGCA CTCCCGAGAG TTGCGCACAC 1200
```

FIG. 1A

```
          1210       1220       1230       1240
     ....|....|  ....|....|  ....|....|  ....|....|
     CTCGAAACGC  GCTGGCCGCC  ATCGGGCTCA  TCTGGGGGCT  1240
     AGCACTGCTC  TTCTCCGGGC  CCTACCTGAG  CTACTACCGT  1280
     CAGTCGCAGC  TGGCCAACCT  GACAGTATGC  CACCCAGCAT  1320
     GGAGCGCACC  TCGACGTCGA  GCCATGGACC  TCTGCACCTT  1360
     CGTCTTTAGC  TACCTGCTGC  CAGTGCTAGT  CCTCAGTCTG  1400
          1410       1420       1430       1440
     ....|....|  ....|....|  ....|....|  ....|....|
     ACCTATGCGC  GTACCCTGCG  CTACCTCTGG  CGCACAGTCG  1440
     ACCCGGTGAC  TGCAGGCTCA  GGTTCCCAGC  GCGCCAAACG  1480
     CAAGGTGACA  CGGATGATCA  TCATCGTGGC  GGTGCTTTTC  1520
     TGCCTCTGTT  GGATGCCCCA  CCACGCGCTT  ATCCTCTGCG  1560
     TGTGGTTTGG  TCGCTTCCCG  CTCACGCGTG  CCACTTACGC  1600
          1610       1620       1630       1640
     ....|....|  ....|....|  ....|....|  ....|....|
     GTTGCGCATC  CTTTCACACC  TAGTTTCCTA  TGCCAACTCC  1640
     TGTGTCAACC  CCATCGTTTA  CGCTCTGGTC  TCCAAGCATT  1680
     TCCGTAAAGG  TTTCCGCAAA  ATCTGCGCGG  GCCTGCTGCG  1720
     CCCTGCCCCG  AGGCGAGCTT  CGGGCCGAGT  GAGCATCCTG  1760
     GCGCCTGGGA  ACCATAGTGG  CAGCATGCTG  GAACAGGAAT  1800
          1810       1820       1830       1840
     ....|....|  ....|....|  ....|....|  ....|....|
     CCACAGACCT  GACACAGGTG  AGCGAGGCAG  CCGGGCCCCT  1840
     TGTCCACCA   CCCGCACTTC  CCAACTGCAC  AGCCTCGAGT  1880
     AGAACCCTGG  ATCCGGCTTG  TTAAAGGACC  AAAGGGCATC  1920
     TAACAGCTTC  TAGACAGTGT  GGCCCGAGGA  TCCCTGGGGG  1960
     TTATGCTTGA  ACGTTACAGG  GTTGAGGCTA  AAGACTGARG  2000
          2010       2020       2030       2040
     ....|....|  ....|....|  ....|....|  ....|....|
     ATTGATTGTA  GGGAACCTCC  AGTTATTAAA  CGGTGCGGAT  2040
     TGCTAGAGGG  TGGCATAGTC  CTTCAATCCT  GGCACCCGAA  2080
     AAGCAGATGC  AGGAGCAGGA  GCAGGAGCAA  AGCCAGCCAT  2120
     GGAGTTTGAG  GCCTGCTTGA  ACTACCTGAG  ATCCAATAAT  2160
     AAAACATTTC  ATATGCTGTG  AAAAAAAAAA  AAAAAAAAAA  2200
```

FIG. 1B

```
          10         20         30         40
    |....|....|....|....|....|....|....|....|
    ATGAATGGCT CCGGCAGCCA GGGCGCGGAG AACACGAGCC   40
    AGGAAGGCGG TAGCGGCGGC TGGCAGCCTG AGGCGGTCCT   80
    TGTACCCCTA TTTTTCGCGC TCATCTTCCT CGTGGGCACC  120
    GTGGGCAACG CGCTGGTGCT GGCGGTGCTG CTGCGCGGCG  160
    GCCAGGCGGT CAGCACCACC AACCTGTTCA TCCTCAACCT  200
         210        220        230        240
    |....|....|....|....|....|....|....|....|
    GGGCGTGGCC GACCTGTGTT TCATCCTGTG CTGCGTGCCT  240
    TTCCAGGCCA CCATCTACAC CCTGGACGAC TGGGTGTTCG  280
    GCTCGCTGCT CTGCAAGGCT GTTCATTCC  TCATCTTTCT  320
    CACTATGCAC GCCAGCAGCT TCACGCTGGC CGCCGTCTCC  360
    CTGGACAGGT AAAGGACCCA GAAAGAAACA TCCAGTATGC  400
         410        420        430        440
    |....|....|....|....|....|....|....|....|
    CCGGAGGGAT CTTGACTGGA AAAGACTGAA TCCTGGTCTG  440
    GTGACCTTAG TTCCCTGCCC TTTCACATCA CTTGGACATT  480
    CCCACAGAAG AGCGGTGAAG AGGCGGTGGT CCTTATTCTC  520
    CTCTGGTTTC CACTGAGTGC AACATGTGCG TCCTGAGTAC  560
    GCTGGAGGGA CTCACAAAAT TTCAGCTTTC TTTAGGAGTT  600
         610        620        630        640
    |....|....|....|....|....|....|....|....|
    TCCTTGCTGT AGTTTGACCC AAGTCTTCTC CAGGTTTCTG  640
    TCAGAACCTC AGGCATGAGG GATCTGCCTC CCCTGGTTGT  680
    CACCAGAGGA TAACAATCAC TGCCCCCAGA AATCCAGACA  720
    GATTCTACAA CTTTTAGTCT TCGGTGTTTT GGGGGTGCCC  760
    CTTCACGTGG AGTAGGTCGG TGCCACATT  CCCAGGAGTG  800
         810        820        830        840
    |....|....|....|....|....|....|....|....|
    ACAATAGCCT AGCAGTGAAT CCTCTCGCTT AGCTGATGCC  840
    CCCCCACTGT CCCCACAGGT ATCTGGCCAT CCGCTACCCG  880
    CTGCACTCCC GAGAGTTGCG CACACCTCGA AACGCGCTGG  920
    CCGCCATCGG GCTCATCTGG GGCTAGCAC  TGCTCTTCTC  960
    CGGGCCCTAC CTGAGCTACT ACCGTCAGTC GCAGCTGGCC 1000
```

FIG. 2A

```
          1010       1020       1030       1040
     |....|....|....|....|....|....|....|....|
     AACCTGACAG TATGCCACCC AGCATGGAGC GCACCTCGAC 1040
     GTCGAGCCAT GGACCTCTGC ACCTTCGTCT TTAGCTACCT 1080
     GCTGCCAGTG CTAGTCCTCA GTCTGACCTA TGCGCGTACC 1120
     CTGCGCTACC TCTGGCGCAC AGTCGACCCG GTGACTGCAG 1160
     GCTCAGGTTC CCAGCGCGCC AAACGCAAGG TGACACGGAT 1200
          1210       1220       1230       1240
     |....|....|....|....|....|....|....|....|
     GATCATCATC GTGGCGGTGC TTTTCTGCCT CTGTTGGATG 1240
     CCCCACCACG CGCTTATCCT CTGCGTGTGG TTTGGTCGCT 1280
     TCCCGCTCAC GCGTGCCACT TACGCGTTGC GCATCCTTTC 1320
     ACACCTAGTT TCCTATGCCA ACTCCTGTGT CAACCCCATC 1360
     GTTACGCTC TGGTCTCCAA GCATTTCCGT AAAGGTTTCC 1400
          1410       1420       1430       1440
     |....|....|....|....|....|....|....|....|
     GCAAAATCTG CGCGGGCCTG CTGCGCCCTG CCCCGAGGCG 1440
     AGCTTCGGGC CGAGTGAGCA TCCTGGCGCC TGGGAACCAT 1480
     AGTGGCAGCA TGCTGGAACA GGAATCCACA GACCTGACAC 1520
     AGGTGAGCGA GGCAGCCGGG CCCCTTGTCC CACCACCCGC 1560
     ACTTCCCAAC TGCACAGCCT CGAGTAGAAC CCTGGATCCG 1600
          1610       1620       1630       1640
     |....|....|....|....|....|....|....|....|
     GCTTGTTAAA GGACCAAAGG GCATCTAACA GCTTCTAGAC 1640
     AGTGTGGCCC GAGGATCCCT GGGGGTTATG CTTGAACGTT 1680
     ACAGGGTTGA GGCTAAAGAC TGAGATTGAT TGTAGGGAAC 1720
     CTCCAGTTAT TAAACGGTGC GGATTGCTAG AGGGTGGCAT 1760
     AGTCCTTCAA TCCTGGCACC CGAAAAGCAG ATGCAGGAGC 1800
          1810       1820       1830       1840
     |....|....|....|....|....|....|....|....|
     AGGAGCAGGA GCAAAGCCAG CCATGGAGTT TGAGGCCTGC 1840
     TTGAACTACC TGAGATCCAA TAATAAAACA TTTCATATGC 1880
     TGTGAAAAAA AAAAAAAAAA AAAA 1904
```

FIG. 2B

```
  1  ATG AAT GGC TCC GGC AGC CAG GGC GCG GAG AAC ACG AGC CAG GAA GGC GGT AGC GGC TGG CAG CCT GAG GCG    75
  1   M   N   G   S   G   S   Q   G   A   E   N   T   S   Q   E   G   G   S   G   W   Q   P   E   A    25

76  GTC CTT GTA CCC CTA TTT TTC GCG CTC ATC CTC GTG GGC ACC GTG TTC CTC AAC CTG TTC CTG GCG CTG          150
 26   V   L   V   P   L   F   F   A   L   I   L   V   G   T   V   F   L   N   L   F   L   A   L         50

151  CTG CGC GGC GGC CAG GCG GTG AGC GCG CAG GCG GTG AAC CTG TTC ATC AAC CTG TTC GAC CTG TGT TTC ATC   225
 51   L   R   G   G   Q   A   V   S   A   Q   A   V   N   L   F   I   N   L   F   D   L   C   F   I    75

226  CTG TGC TGC CCT TTC GTG CAG GCG CCT ATC TAC ACC ATC TAC CTG GAC GAC TGG GGC TCG CTG CTC TGC AAG GCT 300
 76   L   C   C   P   F   V   Q   A   P   I   Y   T   I   Y   L   D   D   W   G   S   L   L   C   K   A 100

301  GTT CAT TTC CTC ATC TTT CTC ACT ATG CAC AGC AGC TTC ACG GCC GCC GTC TCC CTG GAC AG                  368
101   V   H   F   L   I   F   L   T   M   H   S   S   F   T   A   A   V   S   L   D   R                 123

369  gtaaggaccccagaaagaaacatcagtatgcccgagggatcttgactgaatctgctggtgacctt
449  agttccctgcccctgcaacatgtggtacattggacattccacagaagaggccgttgttcctctggtt
529  tccactgagtgcaacatgtgctcctgagtacgctcctgtcctcagctttcttccttct
609  gtagtttgaccaagttctccaggtttgtcagacagattccagaaccctcaggtcatgaggggatcctcaggttgtcaccagag
689  gataacaattcactgcccccagaatccagagattctacaacttttagtcttcggtgttttggggtgccccttcagt
769  ggagtaggtcggtggccacattccaggagtgacaatagcctgcagcagtgaatcctctgcttagctgatgccccccact
849  gtcccccacag 859  G TAT CTG GCC ATC CGC TAC CCG CTG CAC TCC CGA GAG TTG CGC ACA CCT CGA AAC GCG CTG GCC GCC ATC GGG  931
124    Y   L   A   I   R   Y   P   L   H   S   R   E   L   R   T   P   R   N   A   L   A   A   I   G   147

932  CTC ATC TGG GGG CTA GCA CTG CTC CTC TTC TCC GGG CCC TAC CTG AGC CAG TTG CAG CTG GCC AAC CTG        1006
148   L   I   W   G   L   A   L   L   L   F   S   G   P   Y   L   S   Q   L   Q   L   A   N   L          50

1007 ACA GTA TGC CAC CCA GCA GCA TGG AGC GCA CCT CGA CGT CGA ATG GAC CTC TGC TTC GTC TTT AGC TAC CTG   1081
151   T   V   C   H   P   A   A   W   S   A   P   R   R   R   M   D   L   C   F   V   F   S   Y   L   172

1082 CTG CCA GTG CTA GTC CTC AGT CTC ACC TAT GCG CGT CTG CGC TAC CTC TGG CGC ACA GTC GAC CCG GTG ACT  1156
173   L   P   V   L   V   L   S   L   T   Y   A   R   L   R   Y   L   W   R   T   V   D   P   V   T    222
```

FIG. 3A

```
1157  GCA GGC TCA GGT TCC CAG CGC GCC AAA CGC AAG GTG ACA CGG ATG ATC ATC GTG GCG GTG CTT TTC TGC CTC  1231
223    A   G   S   G   S   Q   R   A   K   R   K   V   T   R   M   I   I   V   A   V   L   F   C   L   247

1232  TGT TGG ATG CCC CAC CAC GCG CTT ATC CTC TGC GTG TGG TTT GGT CGC TTC CCG CTC ACG CGT GCC ACT TAC GCG  1306
248    C   W   M   P   H   H   A   L   I   L   C   V   W   F   G   R   F   P   L   T   R   A   T   Y   A   272

1307  TTG CGC ATC CTT TCA CAC CTA GTT TCC TAT GCC AAC TCC TGT GTC AAC CCC ATC GTT TAC GCT CTG GTC TCC AAG  1381
273    L   R   I   L   S   H   L   V   S   Y   A   N   S   C   V   N   P   I   V   Y   A   L   V   S   K   297

1382  CAT TTC CGT AAA GGT TTC CGC AAA ATC TGC GCG GGC CTG CTG CGC CCG AGG CGA GCT TCG GGC CGA GTG  1456
298    H   F   R   K   G   F   R   K   I   C   A   G   L   L   R   P   R   R   A   S   G   R   V   322

1457  AGC ATC CTG GCG CCT GGG AAC CAT AGT GGC AGT ATG CTG GAA CAG GAA TCC ACA GAC CTG ACA CAG GTG AGC GAG  1531
323    S   I   L   A   P   G   N   H   S   G   S   M   L   E   Q   E   S   T   D   L   T   Q   V   S   E   347

1532  GCA GCC GGG CCC CTT GTC CCA CCA GCA CTT CCC AAC TGC ACA GCC TCG AGT AGA ACC CTG GAT CCG GCT TGT  1606
348    A   A   G   P   L   V   P   P   A   L   P   N   C   T   A   S   S   R   T   L   D   P   A   C   372

1607  TAA  1609
       *
```

FIG.3B

```
          10         20         30         40
    |....|....| |....|....| |....|....| |....|....|
MNGSGSQGAE NTSQEGGSGG WQPEAVLVPL FFALIFLVGT  40
VGNALVLAVL LRGGQAVSTT NLFILNLGVA DLCFILCCVP  80
FQATTYTLDD WVFGSLLCKA VHFLIFLTMH ASSFTLAAVS 120
LDRYLAIRYP LHSRELRTPR NALAAIGLIW GLALLFSGPY 160
LSYYRQSQLA NLTVCHPAWS APRRRAMDLC TFVFSYLLPV 200
         210        220        230        240
    |....|....| |....|....| |....|....| |....|....|
LVLSLTYART LRYLWRTVDP VTAGSGSQRA KRKVIRMIII 240
VAVLFCLCWM PHHALILCVW FGRFPLTRAT YALRILSHLV 280
SYANSCVNPI VYALVSKHFR KGFRKICAGL LRPAPRRASG 320
RVSILAPGNH SGSMLEQEST DLTQVSEAAG PLVPPPALPN 360
CTASSRTLDP AC 372
```

FIG. 4

```
ratgal1p     1    M E L A P V N L S E G N G S D P E P P A E P R P L F G I G V E N F      33
ratgal2p     1    - - - - - - M N G G S G Q G A E N T S Q E G G S G G W Q P E A V      26 ratgal1p    34    I T L V F G L I F A M G V L G N S L V I T V L A R S K P G K P R       66
ratgal2p    27    L V P L F F A L I F L F L V G T V G N A L V L L R G - - G Q A V       57 ratgal1p    67    S T T N L F I L N L S I A D L A Y L L F C I P F Q A T V Y A L P T     99
ratgal2p    58    S T T N L F I L N L G V A D L C F I L C C V P F Q A T I Y T L D D     90 ratgal1p   100    W V L G A F I C K F I H Y F F T V S M L V S I F T L A A M S V D R    132
ratgal2p    91    W V F G S L L C K A V H F L I F L T M H A S S F T L A A V S L D R    123 ratgal1p   133    Y V A I V H S R R S S L R V S R N A L L G V G F I W A L S I A M       165
ratgal2p   124    Y L A I R Y P L H S R E L R T P R N A L A A I G L I W G L A L L F    156 ratgal1p   166    A S P V A Y Y Q R L F H R D S N Q T F C W E H W P N Q L H K K A Y    198
ratgal2p   157    S G P Y L S Y Y R Q S Q L - A N L I V C H P A W S A P - R R R A M    187 ratgal1p   199    V V C T F V F G Y L L P L L I C F C Y A K V L N H L H K K L K N      231
ratgal2p   188    D L C T F V F S Y L L P V L V L S L T Y A R T L R Y L W R T V D P    220
```

FIG. 5A

```
ratgal1p  232  M--SKKSEASKKTAQTVLVVVVFGISWLPHH  262
ratgal2p  221  VTAGSGSQRAKRKVTRMIIVAVLFCLCWMPHH  253 ratgal1p  263  VIHLWAEFGAFPLTPASFFFRITAHCLAYSNSS  295
ratgal2p  254  ALILCVWFGRFPLTRATYALRILSHLVSYANSC  286 ratgal1p  296  VNPIIYAFLSENFRKAYKQVFKCRVCNESPHGD  328
ratgal2p  287  VNPIVYALVSKHFRKGFRKICAGLLRPAPRRAS  319 ratgal1p  329  AK------EKNRIDTPPSTNCTHV------  346
ratgal2p  320  GRVSILAPGNHSGSMLEQESTDLTQVSEAAGPL  352 ratgal2p  353  VPPPALPNCTASSRTLDPAC  373
```

FIG. 5B

```
1                                    30
TGCGGACCACCACCAACTTGTACCTGGGCA
                                     60
GCATGGCCGTGTCGACCTACTCATCCTGC
                                     90
TCGGGCTGCCGTTCGACCTGTACCGCCTCT
                                     120
GGCGCTCGCGGCCCTGGGTGTTCGGGCCGC
                                     150
TGCTCTGCCGCCTGTCCCTCTACGTGGGCG
                                     180
AGGGCTGCACCTACGCCACGCTGCTGCACA
                                     210
TGACCGCGCTCAGCGTCGAGCGCTACCTGG
                                     240
CCATCTGCCGCCCGCTCCGCGCCCGCGTCT
                                     270
TGGTCACCCGGCGCCGCGTCCGCGCGCTCA
                                     283
TCGCTGTGCTCTG
```

FIG.6 gagctcggaagcaggtacaagcgccactctccgcctgcgccgtggaatgcgcgccgggacc
antccgcagcccttcccccagcgccgccggccgctgctggggacaacctcgccctcctgtn
tcttgctcctcctcctgaccccagcgcaccccatccccgcccagatgaggcaaggctcc
ctccgccttcagcccggcagagtcgcactaggagttgcagcggccgcagccccgggagctt
cccgctcgcggagacccagacggctgcaggagcccgggcagcctcggggtcagcggcaccA
TGAACGTCTCGGGCTGCCCAGGGGCCGGGAACGCGAGCCAGGCGGGCGGCGGGGGAGGCTG
GCACCCCGAGGCGGTCATCGTGCCCCTGCTCTTCGCGCTCATCTTCCTCGTGGGCACCGTG
GGCAACACGCTGGTGCTGGCGGTGCTGCTGCGCGGCGGCCAGGCGGTCAGCACTACCAACC
TGTTCATCCTTAACCTGGGCGTGGCCGACCTGTGTTTCATCCTGTGCTGCGTGCCCTTCCA
GGCCACCATCTACACCCTGGACGGCTGGGTGTTCGGCTCGCTGCTGTGCAAGGCGGTGCAC
TTCCTCATCTTCCTCACCATGCACGCCAGCAGCTTCACGCTGGCCGCCGTCTCCCTGGACA
Ggtgagccagcgccttggcctccctgggagatgggcatccacgcgggggatggagcgggag
gcgggactggggaccaagaagggacgcgcagagtgggacaggacactaagaaggcagtgga
agacaagcgggcgcggaggaggaaaaagaggaataagaatgggggaccgtggtgtccctcg
gttagatgcgtcctggggcctggaagcctggagaatgtggctctccagcgccgcccgtgcc
tgacaacgcgcagcgtttcccagtacgacgcgtttgtgcgcgttcatctcgcttgagctta
atgccctccgtgagggtgggataggacaaagtgcccaatatacagaagagttgagttccta
agtaactcgctcagagtcgccagccaagggatcgggtgcgttgaagtgaccgtctgtctcc
tgcagccaacttcaggcgcctccactgcgctcgcctccaagccacggttggttggttggt
gcagctggctcaggtccaggctgtggatcttgggtcctttgcaaggatccactccggagtc
ccagcgagcgtgcctaaaggtccctagctcagtcccagcccactctgcctctcgcctccaa
acaaaacaaaaacaaaataaaatccaaaacaagtggggcgggagaggaagcgttgccctgg
ggttcttcctcccagccagaggagagcgaagagacgcacattcgggagagccgccgggact
caggtggagcttgaaaggacactgggatggtttccctggggaggaaatccgggtatttccc
ctctccatcctctggaaaaacagagaggcgaggccagactgcccccacacctcctgtagcc
actgagcgcgaagtgcgttggttccgagcgcgctggtgggatccacaaagctcgcattctc
tcaggaatcccctgagaaattaactgtccccttgcccaacatgtcttctccaggctgtctgc
tagagcctcaggcgcctccgccctccctcccgcggcaccgtcaccagtgggtagtcacagc
ctcccggagcccatagccggttctccaacctttagtcttcagtggctttggggtgccctct
cagtggagactgtggttgcagtccccggggcagcgggagaatggcttgaaggcacaccatt
tcctgctgccggcccgccccatttccagcgtccgctgagtgtctgggacacgctgggaggc
ccccacctccgccctcacgccgagcctcaccccccacctcctctgtgtgcggtgtaaccatg
cgctaaggaccttccttgagagcagccttgggaccgaggtgcagggggtcgcggccctccag
catgaatgtgcccgctcagccgacgtctcccttcccggtctgaccgcagGTATCTGGCCAT
CCGCTACCCGCTGCACTCCCGCGAGCTGCGCACGCCTCGAAACGCGCTGGCAGCCATCGGG
CTCATCTGGGGGCTGTCGCTGCTCTTCTCCGGGCCCTACCTGAGCTACTACCGCCAGTCGC

FIG.7A

AGCTGGCCAACCTGACCGTGTGCCATCCCGCGTGGAGCGCCCCTCGCCGCCGCGCCATGGA
CATCTGCACCTTCGTCTTCAGCTACCTGCTTCCTGTGCTGGTTCTCGGCCTGACCTACGCG
CGCACCTTGCGCTACCTCTGGCGCGCCGTCGACCCGGTGGCCGCGGGCTCGGGTGCCCGGC
GCGCCAAGCGCAAGGTGACACGCATGATCCTCATCGTGGCCGCGCTCTTCTGCCTCTGCTG
GATGCCCCACCACGCGCTCATCCTCTGCGTGTGGTTCGGCCAGTTCCCGCTCACGCGCGCC
ACTTATGCGCTTCGCATCCTCTCGCACCTGGTCTCCTACGCCAACTCCTGCGTCAACCCCA
TCGTTTACGCGCTGGTCTCCAAGCACTTCCGCAAAGGCTTCCGCACGATCTGCGCGGGCCT
GCTGGGCCGTGCCCCAGGCCGAGCCTCGGGCCGTGTGTGCGCTGCCGCGCGGGGCACCCAC
AGTGGCAGCGTGTTGGAGCGCGAGTCCAGCGACCTGTTGCACATGAGCGAGGCGGCGGGGG
CCCTTCGTCCCTGCCCCGGCGCTTCCCAGCCATGCATCCTCGAGCCCTGTCCTGGCCCGTC
CTGGCAGGGCCCAAAGGCAGGCGACAGCATCCTGACGGTTGATGTGGCCTGAaagcactta
gcgggcgcgctgggatgtcacagagttggagtcattgttgggggaccgtggggagagcttt
gcctgttaataaaacgcacaaaccatttcacacacagtgacagcgctgtttcgcgtttctc
attgtcttgagattctgggaggaagcctctggggcttcacagaggggctccctaggggtaa
gtgcaggaccctttgcagagctaccaggaaagagggctgatcacacctcaggcagccggt
tacaatccgcataaaaatctgagtctggggagcgtgcgacagaggcaggcagattgtttaa
ggcgttcgataaagtcggttgatgacagacacagatgtgtgttcccagccgcatttgtgct
ctggtgtgtgacaggtctgtccttgcctgctttcagctcccagggccccttgagtctggg
cagcccagtcagtccccgtccattttggccttagcttttccttccctggctacatctggg
ccaggatcaagtctccagcagctgtttcactcccc

FIG.7B

ATGAACGTCTCGGGCTGCCCAGGGGCCGGGAACGCGAGCCAGGCGGGCGGCGGGGGAGGCT
GGCACCCCGAGGCGGTCATCGTGCCCCTGCTCTTCGCGCTCATCTTCCTCGTGGGCACCGT
GGGCAACACGCTGGTGCTGGCGGTGCTGCTGCGCGGCGGCCAGGCGGTCAGCACTACCAAC
CTGTTCATCCTTAACCTGGGCGTGGCCGACCTGTGTTTCATCCTGTGCTGCGTGCCCTTCC
AGGCCACCATCTACACCCTGGACGGCTGGGTGTTCGGCTCGCTGCTGTGCAAGGCGGTGCA
CTTCCTCATCTTCCTCACCATGCACGCCAGCAGCTTCACGCTGGCCGCCGTCTCCCTGGAC
AGGTATCTGGCCATCCGCTACCCGCTGCACTCCCGCGAGCTGCGCACGCCTCGAAACGCGC
TGGCAGCCATCGGGCTCATCTGGGGGCTGTCGCTGCTCTTCTCCGGGCCCTACCTGAGCTA
CTACCGCCAGTCGCAGCTGGCCAACCTGACCGTGTGCCATCCCGCGTGGAGCGCCCCTCGC
CGCCGCGCCATGGACATCTGCACCTTCGTCTTCAGCTACCTGCTTCCTGTGCTGGTTCTCG
GCCTGACCTACGCGCGCACCTTGCGCTACCTCTGGCGCGCCGTCGACCCGGTGGCCGCGGG
CTCGGGTGCCCGGCGCGCCAAGCGCAAGGTGACACGCATGATCCTCATCGTGGCCGCGCTC
TTCTGCCTCTGCTGGATGCCCCACCACGCGCTCATCCTCTGCGTGTGGTTCGGCCAGTTCC
CGCTCACGCGCGCCACTTATGCGCTTCGCATCCTCTCGCACCTGGTCTCCTACGCCAACTC
CTGCGTCAACCCCATCGTTTACGCGCTGGTCTCCAAGCACTTCCGCAAAGGCTTCCGCACG
ATCTGCGCGGGCCTGCTGGGCCGTGCCCCAGGCCGAGCCTCGGGCCGTGTGTGCGCTGCCG
CGCGGGGCACCCACAGTGGCAGCGTGTTGGAGCGCGAGTCCAGCGACCTGTTGCACATGAG
CGAGGCGGCGGGGGCCCTTCGTCCCTGCCCCGGCGCTTCCCAGCCATGCATCCTCGAGCCC
TGTCCTGGCCCCGTCCTGGCAGGGCCCAAAGGCAGGCGACAGCATCCTGACGGTTGATGTGG
CCTGA

FIG.8

```
gca Ala(A)  2 # cag Gln(Q)  8 # uug Leu(L)  3 # uaa Ter(.)  0
gcc Ala(A) 23 # --- Gln(Q)  8 # --- Leu(L) 56 # uag Ter(.)  0
gcg Ala(A) 19 # gaa Glu(E)  0 # aaa Lys(K)  1 # uga Ter(.)  1
gcu Ala(A)  2 # gag Glu(E)  6 # aag Lys(K)  5 # --- Ter(.)  1
--- Ala(A) 46 # --- Glu(E)  6 # --- Lys(K)  6 # aca Thr(T)  1
aga Arg(R)  0 # gga Gly(G)  1 # aug Met(M)  6 # acc Thr(T) 10
agg Arg(R)  1 # ggc Gly(G) 25 # --- Met(M)  6 # acg Thr(T)  6
cga Arg(R)  2 # ggg Gly(G)  7 # uuc Phe(F) 17 # acu Thr(T)  2
cga Arg(R) 19 # ggu Gly(G)  1 # uuu Phe(F)  0 # --- Thr(T) 19
cgg Arg(R)  2 # --- Gly(G) 34 # --- Phe(F) 17 # ugg Trp(W)  8
cgu Arg(R)  3 # cac His(H) 10 # cca Pro(P)  4 # --- Trp(W)  8
--- Arg(R) 27 # cau His(H)  1 # ccc Pro(P) 10 # uac Tyr(Y) 10
aac Asn(N)  9 # --- His(H) 11 # ccg Pro(P)  4 # uau Tyr(Y)  2
aau Asn(N)  0 # aua Ile(I)  0 # ccu Pro(P)  4 # --- Tyr(Y) 12
--- Asn(N)  9 # auc Ile(I) 18 # --- Pro)P) 22 # gau Val(V)  0
gac Asp(D)  7 # auu Ile(I)  0 # agc Ser(S) 11 # guc Val(V)  9
gau Asp(D)  1 # --- Ile(I) 18 # agu Ser(S)  1 # gug Val(V) 18
--- Asp(D)  8 # cua Leu(L)  0 # uca Ser(S)  0 # guu Val(V)  3
ugc Cys(C) 14 # cuc Leu(L) 17 # ucc Ser(S)  9 # --- Val(V) 30
ugu Cys(C)  2 # cug Leu(L) 32 # ucg Ser(S)  7 # nnn ???(X)  0
--- Cys(C) 16 # cuu Leu(L)  4 # ucu Ser(S)  0 # TOTAL     388
```

FIG.9A

```
MNVSGCPGAGNASQAGGGGGWHPEAVIVPLLFALIFLVGTVGNTL
VLAVLLRGGQAVSTTNLFILNLGVADLCFILCCVPFQATIYTLDGWV
FGSLLCKAVHFLIFLTMHASSFTLAAVSLDRYLAIRYPLHSRELRTPR
NALAAIGLIWGLSLLFSGPYLSYYRQSQLANLTVCHPAWSAPRRRA
MDICTFVFSYLLPVLVLGLTYARTLRYLWRAVDPVAAGSGARRAK
RKVTRMILIVAALFCLCWMPHHALILCVWFGQFPLTRATYALRILS
HLVSYANSCVNPIVYALVSKHFRKGFRTICAGLLGRAPGRASGRVC
AAARGTHSGSVLERESSDLLHMSEAAGALRPCPGASQPCILEPCPGP
SWQGPKAGDSILTVDVA
```

FIG.9B

| Pharmacology of Human and Rat GALR2 $IC_{50}$ (nM) | | | |
|---|---|---|---|
| PEPTIDE | hGALR2 | rat GALR2 | hGALR1* |
| human galanin | 3.8 ± 0.28 | 1.5 ± 0.45 | 0.13 ± 0.04 |
| porcine galanin | 1.5 ± 0.03 | 0.83 ± 0.5 | 0.14 ± 0.04 |
| rat galanin | 1.6 ± 0.42 | 0.9 | 0.1 |
| rat Gal (2-29) | 15.4 ± 7.9 | 2.9 ± 0.9 | 17 ± 7.5 |
| rat Gal (3-29) | >1000 | >1000 | >1000 |
| M40 | 9.5 ± 0.7 | 1.8 ± 1.8 | 0.48 ± 0.2 |
| M35 | 5.6 ± 0.2 | 0.43 ± 0.18 | 0.04 ± 0.02 |
| C7 | 40.5 ± 19 | 13.5 ± 0.7 | 6.3 ± 6.7 |
| Kd | 5 nM | 0.19 nM | 0.07 nM |

FIG.10 gccctttccactttggtgataccATGAATGGCTCGGACAGCCAGGGGGCGGA
GGACTCGAGCCAGGAAGGTGGCGGCGGCTGGCAGCCCGAGGCG
GTCCTCGTACCCCTATTTTTCGCGCTCATCTTCCTCGTGGGCGCTG
TGGGCAACGCGCTGGTGCTGGCGGTGCTGCTGCGCGGCGGCCAG
GCGGTCAGCACCACGAACCTATTCATCCTCAACCTGGGTGTGGC
CGACCTGTGTTTCATCCTGTGCTGCGTGCCTTCCAGGCCACCATC
TATACCCTGGACGATTGGGTGTTTGGCTCACTGCTCTGCAAGGCC
GTTCATTTCCTCATCTTCCTCACTATGCACGCCAGCAGCTTCACGC
TGGCCGCTGTCTCGCTGGACAGgtgagtgaacattctgtggtgtctgagaactgggt
acccaggtaggagcttgcactggagtcgccacgcaaggatccagaagggatgcgtagtcggggag
aacactaaaattacaaagtggcccgaggccgtgaaacgcaaggggaaaggggactaagactccg
tgactaagagtgtcccttgattaagtcggtcctcagacctcgaaggctggagaaatcggatttctgggg
tctttacgttattgttgcttgagctaaaagtctctcagaaacattgcagtactcagaccagagttggcttg
caaagtaacttgccagtattcaaatgctaattgagagctgcagagaggcatttgcttcttggccccaag
ctcagcacctggagcgttgtccggctttaggcttaggactgagctgtactttggatagacccatgctga
agtccaaggcagcgggagtgagggctcctagcggacgtctaaagccttccaggccaaggctccccg
cccggagacgcctgcggtttgatgttccttccctagctaaaggacccagaaagagaaacttccagaat
gctctgaaggactcgtgactggaaaagacactagaaacaggtcctgggaaggatgtcattagttccc
tgccccttcgcatcacttggcccttcccacagtagagcggtgaagagaggcggagatcctcattctctg
ctttccactgagtgcaacatgtgggttctgagtccgctggtgggacgcacaaaacttcagctttcttcag
ggatttccttgctctacccaagtcttctccgggttgtctgtcagagagcctcaggcattagagatttgtctc
cctcggttgtcacaagaggataataatcactgcccccagaagtcctggcatattctacaacttttagtttt
cggtggtttggggatgccctttcgcgtggtaggtcagtggccacattctcagggttggtaatggtctagc
agtgaattagtgaatcctttcgcttacctgtcgtcgtcgtccccccgccccactgtccactcagGTAT
CTGGCCATCCGCTACCCGATGCACTCCCGAGAGTTGCGCACACCT
CGAAACGCGCTGGCGGCCATCGGGCTCATCTGGGGGCTAGCACT
GCTCTTCTCCGGGCCCTACCTGAGCTACTACAGTCAGTCGCAGCT
GGCCAATCTGACGGTGTGCCACCCAGCGTGGAGCGCACCACGAC
GTCGCGCCATGGACCTCTGCACTTTTGTCTTTAGCTACCTGTTGCC
AGTGCTGGTGCTCAGCCTGACCTATGCGCGCACCCTGCACTACCT
CTGGCGCACAGTTGACCCAGTAGCTGCAGGCTCAGGTTCCCAGC
GCGCCAAGCGCAAGGTGACACGGATGATCGTCATCGTGGCGGTA
CTCTTCTGCCTCTGTTGGATGCCCCACCACGCGCTTATCCTCTGCG
TGTGGTTTGGTCGCTTTCCGCTCACGCGTGCCACTTACGCCCTGC
GCATCCTTTCACATCTAGTATCTTATGCCAACTCGTGTGTCAACCC
CATCGTTTATGCTCTGGTCTCCAAGCATTTCCGCAAAGGTTTCCG
CAAAATCTGCGCGGGCCTGCTACGCCGTGCCCCGAGGAGAGCTT
CAGGCCGAGTGTGCATCCTGGCGCCTGGAAACCATAGTGGTGGC
ATGCTGGAACCTGAGTCCACAGACCTGACACAGGTGAGCGAGG
CAGCCGGGCCCCTCGTCCCCGCACCCGCACTTCCCAACTGCACA
ACCTTGAGTAGAACCCTCGATCCAGCCTGTTAAaggaccaaagggcatct
aacagcttctaagggcga

FIG. 12

MNGSDSQGAEDSSQEGGGGWQPEAVLVPLFFALIFLVGAVGNALVL
AVLLRGGQAVSTTNLFILNLGVADLCFILCCVPFQATIYTLDDWVFG
SLLCKAVHFLIFLTMHASSFTLAAVSLDRYLAIRYPMHSRELRTPRN
ALAAIGLIWGLALLFSGPYLSYYSQSQLANLTVCHPAWSAPRRRAM
DLCTFVFSYLLP VLVLSLTYARTLHYLWRTVDPVAAGSGSQRAKRK
VTRMIVIVAVLF CLCWMPHHALILCVWFGRFPLTRATYALRILSHL
VSYANSCVNPIVYALVSKHFRKGFRKICAGLLRRAPRRASGRVCIL
APGNHSGGMLEPESTDLTQVSEAAGPLVPAPALPNCTTLSRTLDPAC

| | | | | | | | | | | | | | | | | | | | | | |
|---|---|---|---|---|---|---|---|---|---|---|---|---|---|---|---|---|---|---|---|---|---|
| mGALR1 130 | S | V | D | R | Y | V | A | I | V | H | S | R | R | S | S | L | R | V | S | P | R | N | A | L | L | G | V | G | F | I | W | A | L | 162 |
| rGALR1 129 | S | V | D | R | Y | V | A | I | V | H | S | R | R | S | S | L | R | V | S | P | R | N | A | L | L | G | V | G | F | I | W | A | L | 161 |
| hGALR1 130 | S | V | D | R | Y | V | A | I | V | H | S | R | R | S | S | L | R | V | S | P | R | N | A | L | L | G | V | G | C | I | W | A | L | 162 |
| mGALR2 119 | S | L | D | R | Y | L | A | I | R | Y | P | L | H | S | R | E | L | R | T | P | R | N | A | L | A | A | I | G | L | I | W | G | L | 151 |
| rGALR2 120 | S | L | D | R | Y | L | A | I | R | Y | P | L | H | S | R | E | L | R | T | P | R | N | A | L | A | A | I | G | L | I | W | G | L | 152 |
| hGALR2 120 | S | L | D | R | Y | L | A | I | R | Y | P | L | H | S | R | E | L | R | T | P | R | N | A | L | A | A | I | G | L | I | W | G | L | 152 |

| | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| mGALR1 163 | S | I | A | M | A | S | P | V | A | Y | H | Q | R | L | F | H | - | R | D | S | N | Q | T | F | C | W | E | Q | W | P | N | K | L | 194 |
| rGALR1 162 | S | I | A | M | A | S | P | V | A | Y | Y | Q | R | L | F | H | - | R | D | S | N | Q | T | F | C | W | E | Q | W | P | D | P | R | 193 |
| hGALR1 163 | S | I | A | M | A | S | P | V | A | Y | H | Q | G | L | F | H | P | R | A | S | N | Q | T | F | C | W | E | H | W | P | D | A | R | 195 |
| mGALR2 152 | A | L | L | F | S | G | P | - | - | Y | L | S | Y | Y | S | Q | S | Q | L | A | N | L | T | V | C | H | P | A | W | S | A | P | R | 182 |
| rGAL2 153 | A | L | L | F | S | G | P | - | - | Y | L | S | Y | Y | R | Q | S | Q | L | A | N | L | T | V | C | H | P | A | W | S | A | P | R | 183 |
| hGALR2 153 | S | L | L | F | S | G | P | - | - | Y | L | S | Y | Y | R | Q | S | Q | L | A | N | L | T | V | C | H | P | A | W | S | A | P | R | 183 |

| | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| mGALR1 195 | H | K | K | A | Y | V | V | C | T | F | V | F | G | Y | L | L | P | L | L | L | I | C | F | C | Y | A | K | V | L | N | H | L | H | 227 |
| rGALR1 194 | H | K | K | A | Y | V | V | C | T | F | V | F | G | Y | L | L | P | L | L | L | I | C | F | C | Y | A | K | V | L | N | H | L | H | 226 |
| hGALR1 196 | H | K | K | A | Y | V | V | C | T | F | V | F | G | Y | L | L | P | L | L | L | I | C | F | C | Y | A | K | V | L | N | H | L | H | 228 |
| mGALR2 183 | R | R | - | A | M | D | L | C | T | F | V | F | S | Y | L | L | P | V | L | V | L | S | L | T | Y | A | R | T | L | R | Y | L | W | 214 |
| rGALR2 184 | R | R | - | I | A | M | D | L | C | T | F | V | F | S | Y | L | L | P | V | L | V | L | S | L | T | Y | A | R | T | L | R | Y | L | W | 215 |
| hGALR2 184 | R | R | - | A | M | D | I | C | T | F | V | F | S | Y | L | L | P | V | L | G | L | T | Y | A | R | T | L | R | Y | L | W | 215 |

FIG.14C

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| mGALR1 | 347 | H | V | – | – | – | – | – | – | – | – | – | – | – | – | – | – | – | – | – | – | – | – | – | – | – | – | – | – | 348 |
| rGALR1 | 345 | H | V | – | – | – | – | – | – | – | – | – | – | – | – | – | – | – | – | – | – | – | – | – | – | – | – | – | – | 346 |
| hGALR1 | 348 | H | V | – | – | – | – | – | – | – | – | – | – | – | – | – | – | – | – | – | – | – | – | – | – | – | – | – | – | 349 |
| mGALR2 | 343 | Q | V | S | E | A | A | G | P | L | V | P | A | P | A | – | – | L | P | N | C | T | T | L | S | R | T | L | D | P | 369 |
| rGALR2 | 344 | Q | V | S | E | A | A | G | P | L | V | P | P | P | A | – | – | L | P | N | C | T | A | S | S | R | T | L | D | P | 370 |
| hGALR2 | 344 | H | M | S | E | A | A | G | A | L | R | P | C | P | G | A | S | Q | P | C | I | L | E | P | C | P | G | P | S | W | Q | G | P | K | 376 |

| | | | |
|---|---|---|---|
| mGALR1 | 0 | – | – | 0 |
| rGALR1 | 0 | – | – | 0 |
| hGALR1 | 0 | – | – | 0 |
| mGALR2 | 370 | A | C | 371 |
| rGALR2 | 371 | A | C | 372 |
| hGALR2 | 377 | A G D S I L T V D V A | | 387 |

FIG. 14D

| Tissue | Expression Level | Tissue | Expression Level |
|---|---|---|---|
| Total Brain | + | Prostate | +++ |
| Cerebellum | + | Thymus | ++ |
| Cerebral Cortex | + | Spleen | + |
| Medulla | + | Pancreas | + |
| Occipital Pole | + | Placenta | ++ |
| Frontal Pole | + | Heart | - |
| Temporal Lobe | + | Lung | - |
| Putamen | + | Liver | - |
| Spinal Cord | + | Skeletal muscle | - |
| Amygdala | + | Kidney | - |
| Caudate Nucleus | + | Testis | - |
| Corpus Callosum | + | Ovary | - |
| Hippocampus | + | Small intestine | - |
| Substantia Nigra | + | Colon | - |
| Subthalamic n. | + | Blood Leukocyte | - |
| Thalamus | + | | |

FIG. 15

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 2200 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
CGCTCCCTCC ACACCTCCAG GGGCAGTGAG CCACTCAAGT CTAAAGCAGA GCGAGTCCCA    60
GGACTTGAGC GCGGGAAGCG AATGGAGTCA GGGTCATTCG ATTGCACCTC TCTCGGCTGC   120
GGGCCGGAGC GGGGTACCAT CCTACACTCT GGGTGCTCCC TCCTCCTCCC GTCCCCCGCG   180
CACCCCTGCC CTGGCTCCTG GAGCTCGGCA GTCTCGCTGG GGCGCTGCAG CGAGGGAGCA   240
GCGTGCTCAC CAAGACCCGG ACAGCTGCGG GAGCGGCGTC CACTTTGGTG ATACCATGAA   300
TGGCTCCGGC AGCCAGGGCG CGGAGAACAC GAGCCAGGAA GGCGGTAGCG GCGGCTGGCA   360
GCCTGAGGCG GTCCTTGTAC CCCTATTTTT CGCGCTCATC TTCCTCGTGG GCACCGTGGG   420
CAACGCGCTG GTGCTGGCGG TGCTGCTGCG CGGCGGCCAG GCGGTCAGCA CCACCAACCT   480
GTTCATCCTC AACCTGGGCG TGGCCGACCT GTGTTTCATC CTGTGCTGCG TGCCTTTCCA   540
GGCCACCATC TACACCCTGG ACGACTGGGT GTTCGGCTCG CTGCTCTGCA AGGCTGTTCA   600
TTTCCTCATC TTTCTCACTA TGCACGCCAG CAGCTTCACG CTGGCCGCCG TCTCCCTGGA   660
CAGGTAAAGG ACCCAGAAAG AAACATCCAG TATGCCCGGA GGGATCTTGA CTGGAAAAGA   720
CTGAATCCTG GTCTGGTGAC CTTAGTTCCC TGCCCTTTCA CATCACTTGG ACATTCCCAC   780
AGAAGAGCGG TGAAGAGGCG GTGGTCCTTA TTCTCCTCTG GTTTCCACTG AGTGCAACAT   840
GTGCGTCCTG AGTACGCTGG AGGGACTCAC AAAATTTCAG CTTTCTTTAG GAGTTTCCTT   900
GCTGTAGTTT GACCCAAGTC TTCTCCAGGT TTCTGTCAGA ACCTCAGGCA TGAGGGATCT   960
GCCTCCCCTG GTTGTCACCA GAGGATAACA ATCACTGCCC CCAGAAATCC AGACAGATTC  1020
TACAACTTTT AGTCTTCGGT GTTTTGGGGG TGCCCCTTCA CGTGGAGTAG GTCGGTGGCC  1080
ACATTCCCAG GAGTGACAAT AGCCTAGCAG TGAATCCTCT CGCTTAGCTG ATGCCCCCCC  1140
ACTGTCCCCA CAGGTATCTG GCCATCCGCT ACCCGCTGCA CTCCCGAGAG TTGCGCACAC  1200
CTCGAAACGC GCTGGCCGCC ATCGGGCTCA TCTGGGGGCT AGCACTGCTC TTCTCCGGGC  1260
CCTACCTGAG CTACTACCGT CAGTCGCAGC TGGCCAACCT GACAGTATGC CACCCAGCAT  1320
GGAGCGCACC TCGACGTCGA GCCATGGACC TCTGCACCTT CGTCTTTAGC TACCTGCTGC  1380
CAGTGCTAGT CCTCAGTCTG ACCTATGCGC GTACCCTGCG CTACCTCTGG CGCACAGTCG  1440
ACCCGGTGAC TGCAGGCTCA GGTTCCCAGC GCGCCAAACG CAAGGTGACA CGGATGATCA  1500
TCATCGTGGC GGTGCTTTTC TGCCTCTGTT GGATGCCCCA CCACGCGCTT ATCCTCTGCG  1560
TGTGGTTTGG TCGCTTCCCG CTCACGCGTG CCACTTACGC GTTGCGCATC CTTTCACACC  1620
TAGTTTCCTA TGCCAACTCC TGTGTCAACC CCATCGTTTA CGCTCTGGTC TCCAAGCATT  1680
TCCGTAAAGG TTTCCGCAAA ATCTGCGCGG GCCTGCTGCG CCCTGCCCCG AGGCGAGCTT  1740
CGGGCCGAGT GAGCATCCTG GCGCCTGGGA ACCATAGTGG CAGCATGCTG GAACAGGAAT  1800
```

```
CCACAGACCT GACACAGGTG AGCGAGGCAG CCGGGCCCCT TGTCCCACCA CCCGCACTTC    1860

CCAACTGCAC AGCCTCGAGT AGAACCCTGG ATCCGGCTTG TTAAAGGACC AAAGGGCATC    1920

TAACAGCTTC TAGACAGTGT GGCCCGAGGA TCCCTGGGGG TTATGCTTGA ACGTTACAGG    1980

GTTGAGGCTA AAGACTGARG ATTGATTGTA GGGAACCTCC AGTTATTAAA CGGTGCGGAT    2040

TGCTAGAGGG TGGCATAGTC CTTCAATCCT GGCACCCGAA AAGCAGATGC AGGAGCAGGA    2100

GCAGGAGCAA AGCCAGCCAT GGAGTTTGAG GCCTGCTTGA ACTACCTGAG ATCCAATAAT    2160

AAAACATTTC ATATGCTGTG AAAAAAAAAA AAAAAAAAA                           2200
```

(2) INFORMATION FOR SEQ ID NO:2:

(i) SEQUENCE CHARACTERISTICS:
        (A) LENGTH: 372 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Asn Gly Ser Gly Ser Gln Gly Ala Glu Asn Thr Ser Gln Glu Gly
 1               5                  10                  15

Gly Ser Gly Gly Trp Gln Pro Glu Ala Val Leu Val Pro Leu Phe Phe
                20                  25                  30

Ala Leu Ile Phe Leu Val Gly Thr Val Gly Asn Ala Leu Val Leu Ala
            35                  40                  45

Val Leu Leu Arg Gly Gly Gln Ala Val Ser Thr Thr Asn Leu Phe Ile
        50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Asp Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ala Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Ala Met Asp Leu Cys Thr Phe
            180                 185                 190

Val Phe Ser Tyr Leu Leu Pro Val Leu Val Leu Ser Leu Thr Tyr Ala
        195                 200                 205

Arg Thr Leu Arg Tyr Leu Trp Arg Thr Val Asp Pro Val Thr Ala Gly
    210                 215                 220

Ser Gly Ser Gln Arg Ala Lys Arg Lys Val Thr Arg Met Ile Ile Ile
225                 230                 235                 240

Val Ala Val Leu Phe Cys Leu Cys Trp Met Pro His His Ala Leu Ile
                245                 250                 255

Leu Cys Val Trp Phe Gly Arg Phe Pro Leu Thr Arg Ala Thr Tyr Ala
            260                 265                 270
```

```
Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
        290                 295                 300

Lys Ile Cys Ala Gly Leu Leu Arg Pro Ala Pro Arg Arg Ala Ser Gly
305                     310                 315                 320

Arg Val Ser Ile Leu Ala Pro Gly Asn His Ser Gly Ser Met Leu Glu
                325                 330                 335

Gln Glu Ser Thr Asp Leu Thr Gln Val Ser Glu Ala Ala Gly Pro Leu
            340                 345                 350

Val Pro Pro Pro Ala Leu Pro Asn Cys Thr Ala Ser Ser Arg Thr Leu
        355                 360                 365

Asp Pro Ala Cys
        370

(2) INFORMATION FOR SEQ ID NO:3:

(i) SEQUENCE CHARACTERISTICS:
        (A) LENGTH: 346 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Glu Leu Ala Pro Val Asn Leu Ser Glu Gly Asn Gly Ser Asp Pro
1               5                   10                  15

Glu Pro Pro Ala Glu Pro Arg Pro Leu Phe Gly Ile Gly Val Glu Asn
            20                  25                  30

Phe Ile Thr Leu Val Val Phe Gly Leu Ile Phe Ala Met Gly Val Leu
        35                  40                  45

Gly Asn Ser Leu Val Ile Thr Val Leu Ala Arg Ser Lys Pro Gly Lys
    50                  55                  60

Pro Arg Ser Thr Thr Asn Leu Phe Ile Leu Asn Leu Ser Ile Ala Asp
65                  70                  75                  80

Leu Ala Tyr Leu Leu Phe Cys Ile Pro Phe Gln Ala Thr Val Tyr Ala
                85                  90                  95

Leu Pro Thr Trp Val Leu Gly Ala Phe Ile Cys Lys Phe Ile His Tyr
            100                 105                 110

Phe Phe Thr Val Ser Met Leu Val Ser Ile Phe Thr Leu Ala Ala Met
        115                 120                 125

Ser Val Asp Arg Tyr Val Ala Ile Val His Ser Arg Arg Ser Ser Ser
    130                 135                 140

Leu Arg Val Ser Arg Asn Ala Leu Leu Gly Val Gly Phe Ile Trp Ala
145                 150                 155                 160

Leu Ser Ile Ala Met Ala Ser Pro Val Ala Tyr Tyr Gln Arg Leu Phe
                165                 170                 175

His Arg Asp Ser Asn Gln Thr Phe Cys Trp Glu His Trp Pro Asn Gln
            180                 185                 190

Leu His Lys Lys Ala Tyr Val Val Cys Thr Phe Val Phe Gly Tyr Leu
        195                 200                 205

Leu Pro Leu Leu Leu Ile Cys Phe Cys Tyr Ala Lys Val Leu Asn His
    210                 215                 220

Leu His Lys Lys Leu Lys Asn Met Ser Lys Ser Glu Ala Ser Lys
225                 230                 235                 240
```

```
Lys Lys Thr Ala Gln Thr Val Leu Val Val Val Val Phe Gly Ile
            245                 250                 255

Ser Trp Leu Pro His His Val Ile His Leu Trp Ala Glu Phe Gly Ala
            260                 265                 270

Phe Pro Leu Thr Pro Ala Ser Phe Phe Arg Ile Thr Ala His Cys
            275                 280                 285

Leu Ala Tyr Ser Asn Ser Ser Val Asn Pro Ile Ile Tyr Ala Phe Leu
            290                 295                 300

Ser Glu Asn Phe Arg Lys Ala Tyr Lys Gln Val Phe Lys Cys Arg Val
305                 310                 315                 320

Cys Asn Glu Ser Pro His Gly Asp Ala Lys Glu Lys Asn Arg Ile Asp
                325                 330                 335

Thr Pro Pro Ser Thr Asn Cys Thr His Val
            340                 345
```

(2) INFORMATION FOR SEQ ID NO:4:

(i) SEQUENCE CHARACTERISTICS:
        (A) LENGTH: 283 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...283
        (D) OTHER INFORMATION: cDNA probe (xi) SEQUENCE DESCRIPTION: SEQ ID NO:4:

```
TGCGGACCAC CACCAACTTG TACCTGGGCA GCATGGCCGT GTCCGACCTA CTCATCCTGC      60
TCGGGCTGCC GTTCGACCTG TACCGCCTCT GGCGCTCGCG GCCCTGGGTG TTCGGGCCGC     120
TGCTCTGCCG CCTGTCCCTC TACGTGGGCG AGGGCTGCAC CTACGCCACG CTGCTGCACA     180
TGACCGCGCT CAGCGTCGAG CGCTACCTGG CCATCTGCCG CCCGCTCCGC GCCCGCGTCT     240
TGGTCACCCG GCGCCGCGTC CGCGCGCTCA TCGCTGTGCT CTG                       283
```

(2) INFORMATION FOR SEQ ID NO:5:

(i) SEQUENCE CHARACTERISTICS:
        (A) LENGTH: 3390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Other
        (B) LOCATION: 63...63
        (D) OTHER INFORMATION: N = A, C, T or G
        (A) NAME/KEY: Other
        (B) LOCATION: 122...122
        (D) OTHER INFORMATION: N = A, C, T or G (xi) SEQUENCE DESCRIPTION: SEQ ID NO:5:

```
GAGCTCGGAA GCAGGTACAA GCGCCACTCT CCGCCTGCGC CGTGGAATGC GCGCCGGGAC      60
CANTCCGCAG CCCTTCCCCC AGCGCCGCCG GCCGCTGCTG GGGACAACCT CGCCCTCCTG     120
TNTCTTGCTC CTCCTCCTGA CCCCAGCGCA CCCCCATCCC CGCCCCAGAT GAGGCAAGGC     180
TCCCTCCGCC TTCAGCCCGG CAGAGTCGCA CTAGGAGTTG CAGCGGCCGC AGCCCCGGGA     240
GCTTCCCGCT CGCGGAGACC CAGACGGCTG CAGGAGCCCG GGCAGCCTCG GGGTCAGCGG     300
```

```
CACCATGAAC GTCTCGGGCT GCCCAGGGGC CGGGAACGCG AGCCAGGCGG GCGGCGGGGG    360
AGGCTGGCAC CCCGAGGCGG TCATCGTGCC CCTGCTCTTC GCGCTCATCT TCCTCGTGGG    420
CACCGTGGGC AACACGCTGG TGCTGGCGGT GCTGCTGCGC GGCGGCCAGG CGGTCAGCAC    480
TACCAACCTG TTCATCCTTA ACCTGGGCGT GGCCGACCTG TGTTTCATCC TGTGCTGCGT    540
GCCCTTCCAG GCCACCATCT ACACCCTGGA CGGCTGGGTG TTCGGCTCGC TGCTGTGCAA    600
GGCGGTGCAC TTCCTCATCT TCCTCACCAT GCACGCCAGC AGCTTCACGC TGGCCGCCGT    660
CTCCCTGGAC AGGTGAGCCA GCGCCTTGGC CTCCCTGGGA GATGGGCATC CACGCGGGGG    720
ATGGAGCGGG AGGCGGGACT GGGGACCAAG AAGGGACGCG CAGAGTGGGA CAGGACACTA    780
AGAAGGCAGT GGAAGACAAG CGGGCGCGGA GGAGGAAAAA GAGGAATAAG AATGGGGGAC    840
CGTGGTGTCC CTCGGTTAGA TGCGTCCTGG GGCCTGGAAG CCTGGAGAAT GTGGCTCTCC    900
AGCGCCGCCC GTGCCTGACA ACGCGCAGCG TTTCCCAGTA CGACGCGTTT GTGCGCGTTC    960
ATCTCGCTTG AGCTTAATGC CCTCCGTGAG GGTGGGATAG ACAAAGTGC CCAATATACA    1020
GAAGAGTTGA GTTCCTAAGT AACTCGCTCA GAGTCGCCAG CCAAGGGATC GGGTGCGTTG    1080
AAGTGACCGT CTGTCTCCTG CAGCCAACTT CAGGCGCCTC CACTGCGCTC GCCTCCAAGC    1140
CACGGTTTGG TTGGTTGGTG CAGCTGGCTC AGGTCCAGGC TGTGGATCTT GGGTCCTTTG    1200
CAAGGATCCA CTCCGGAGTC CCAGCGAGCG TGCCTAAAGG TCCCTAGCTC AGTCCCAGCC    1260
CACTCTGCCT CTCGCCTCCA AACAAAACAA AAACAAAATA AAATCCAAAA CAAGTGGGGC    1320
GGGAGAGGAA GCGTTGCCCT GGGGTTCTTC CTCCCAGCCA GAGGAGAGCG AAGAGACGCA    1380
CATTCGGGAG AGCCGCCGGG ACTCAGGTGG AGCTTGAAAG GACACTGGGA TGGTTTCCCT    1440
GGGGAGGAAA TCCGGGTATT TCCCCTCTCC ATCCTCTGGA AAAACAGAGA GGCGAGGCCA    1500
GACTGCCCCC ACACCTCCTG TAGCCACTGA GCGCGAAGTG CGTTGGTTCC GAGCGCGCTG    1560
GTGGGATCCA CAAAGCTCGC ATTCTCTCAG GAATCCCCTG AGAAATTAAC TGTCCCTTGC    1620
CCAACATGTC TTCTCCAGGC TGTCTGCTAG AGCCTCAGGC GCCTCCGCCC TCCTCCCGC    1680
GGCACCGTCA CCAGTGGGTA GTCACAGCCT CCCGGAGCCC ATAGCCGGTT CTCCAACCTT    1740
TAGTCTTCAG TGGCTTTGGG GTGCCCTCTC AGTGGAGACT GTGGTTGCAG TCCCCGGGGG    1800
CAGCGGGAGA ATGGCTTGAA GGCACACCTT TCCTGCTGCC GGCCCGCCCC ATTTCCAGCG    1860
TCCGCTGAGT GTCTGGGACA CGCTGGGAGG CCCCCACCTC CGCCCTCACG CCGAGCCTCA    1920
CCCCCACCTC CTCTGTGTGC GGTGTAACCA TGCGCTAAGG ACCTTCCTTG AGAGCAGCCT    1980
TGGGACCGAG GTGCAGGGGT CGCGGCCCTC CAGCATGAAT GTGCCCGCTC AGCCGACGTC    2040
TCCCTTCCCG GTCTGACCGC AGGTATCTGG CCATCCGCTA CCCGCTGCAC TCCCGCGAGC    2100
TGCGCACGCC TCGAAACGCG CTGGCAGCCA TCGGGCTCAT CTGGGGGCTG TCGCTGCTCT    2160
TCTCCGGGCC CTACCTGAGC TACTACCGCC AGTCGCAGCT GGCCAACCTG ACCGTGTGCC    2220
ATCCCGCGTG GAGCGCCCCT CGCCGCCGCG CCATGGACAT CTGCACCTTC GTCTTCAGCT    2280
ACCTGCTTCC TGTGCTGGTT CTCGGCCTGA CCTACGCGCG CACCTTGCGC TACCTCTGGC    2340
GCGCCGTCGA CCCGGTGGCC GCGGGCTCGG GTGCCCGGCG CGCCAAGCGC AAGGTGACAC    2400
GCATGATCCT CATCGTGGCC GCGCTCTTCT GCCTCTGCTG GATGCCCCAC CACGCGCTCA    2460
TCCTCTGCGT GTGGTTCGGC CAGTTCCCGC TCACGCGCGC CACTTATGCG CTTCGCATCC    2520
TCTCGCACCT GGTCTCCTAC GCCAACTCCT GCGTCAACCC CATCGTTTAC GCGCTGGTCT    2580
CCAAGCACTT CCGCAAAGGC TTCCGCACGA TCTGCGCGGG CCTGCTGGGC CGTGCCCCAG    2640
```

-continued

```
GCCGAGCCTC GGGCCGTGTG TGCGCTGCCG CGCGGGGCAC CCACAGTGGC AGCGTGTTGG      2700

AGCGCGAGTC CAGCGACCTG TTGCACATGA GCGAGGCGGC GGGGGCCCTT CGTCCCTGCC      2760

CCGGCGCTTC CCAGCCATGC ATCCTCGAGC CCTGTCCTGG CCCGTCCTGG CAGGGCCCAA      2820

AGGCAGGCGA CAGCATCCTG ACGGTTGATG TGGCCTGAAA GCACTTAGCG GGCGCGCTGG      2880

GATGTCACAG AGTTGGAGTC ATTGTTGGGG ACCGTGGGG AGAGCTTTGC CTGTTAATAA       2940

AACGCACAAA CCATTTCACA CACAGTGACA GCGCTGTTTC GCGTTTCTCA TTGTCTTGAG      3000

ATTCTGGGAG GAAGCCTCTG GGGCTTCACA GAGGGGCTCC CTAGGGGTAA GTGCAGGACC      3060

CTTTGCAGAG CTACCAGGAA AGAGGGCTGA TCACACCTCA GGCAGCCGGG TTACAATCCG      3120

CATAAAAATC TGAGTCTGGG GAGCGTGCGA CAGAGGCAGG CAGATTGTTT AAGGCGTTCG      3180

ATAAAGTCGG TTGATGACAG ACACAGATGT GTGTTCCCAG CCGCATTTGT GCTCTGGTGT      3240

GTGACAGGTC TGTCCTTGCC TGCTTTCAGC TCCCAGGGCC CCTTTGAGTC TGGGCAGCCC      3300

AGTCAGTCCC CGTCCATTTT TGGCCTTAGC TTTTCCTTCC CTGGCTACAT CTGGGCCAGG      3360

ATCAAGTCTC CAGCAGCTGT TTCACTCCCC                                      3390

(2) INFORMATION FOR SEQ ID NO:6:

(i) SEQUENCE CHARACTERISTICS:
        (A) LENGTH: 1164 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

ATGAACGTCT CGGGCTGCCC AGGGGCCGGG AACGCGAGCC AGGCGGGCGG CGGGGGAGGC        60

TGGCACCCCG AGGCGGTCAT CGTGCCCCTG CTCTTCGCGC TCATCTTCCT CGTGGGCACC       120

GTGGGCAACA CGCTGGTGCT GGCGGTGCTG CTGCGCGGCG GCCAGGCGGT CAGCACTACC       180

AACCTGTTCA TCCTTAACCT GGGCGTGGCC GACCTGTGTT TCATCCTGTG CTGCGTGCCC       240

TTCCAGGCCA CCATCTACAC CCTGGACGGC TGGGTGTTCG GCTCGCTGCT GTGCAAGGCG       300

GTGCACTTCC TCATCTTCCT CACCATGCAC GCCAGCAGCT TCACGCTGGC CGCCGTCTCC       360

CTGGACAGGT ATCTGGCCAT CCGCTACCCG CTGCACTCCC GCGAGCTGCG CACGCCTCGA       420

AACGCGCTGG CAGCCATCGG GCTCATCTGG GGGCTGTCGC TGCTCTTCTC CGGGCCCTAC       480

CTGAGCTACT ACCGCCAGTC GCAGCTGGCC AACCTGACCG TGTGCCATCC CGCGTGGAGC       540

GCCCCTCGCC GCCGCGCCAT GGACATCTGC ACCTTCGTCT TCAGCTACCT GCTTCCTGTG       600

CTGGTTCTCG GCCTGACCTA CGCGCGCACC TTGCGCTACC TCTGGCGCGC CGTCGACCCG       660

GTGGCCGCGG GCTCGGGTGC CCGGCGCGCC AAGCGCAAGG TGACACGCAT GATCCTCATC       720

GTGGCCGCGC TCTTCTGCCT CTGCTGGATG CCCCACCACG CGCTCATCCT CTGCGTGTGG       780

TTCGGCCAGT TCCCGCTCAC GCGCGCCACT TATGCGCTTC GCATCCTCTC GCACCTGGTC       840

TCCTACGCCA ACTCCTGCGT CAACCCCATC GTTTACGCGC TGGTCTCCAA GCACTTCCGC       900

AAAGGCTTCC GCACGATCTG CGCGGGCCTG CTGGGCCGTG CCCCAGGCCG AGCCTCGGGC       960

CGTGTGTGCG CTGCCGCGCG GGGCACCCAC AGTGGCAGCG TGTTGGAGCG CGAGTCCAGC      1020

GACCTGTTGC ACATGAGCGA GGCGGCGGGG GCCCTTCGTC CCTGCCCCGG CGCTTCCCAG      1080

CCATGCATCC TCGAGCCCTG TCCTGGCCCG TCCTGGCAGG GCCCAAAGGC AGGCGACAGC      1140

ATCCTGACGG TTGATGTGGC CTGA                                            1164
```

(2) INFORMATION FOR SEQ ID NO:7:

(i) SEQUENCE CHARACTERISTICS:
        (A) LENGTH: 387 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Asn Val Ser Gly Cys Pro Gly Ala Gly Asn Ala Ser Gln Ala Gly
 1               5                  10                  15

Gly Gly Gly Gly Trp His Pro Glu Ala Val Ile Val Pro Leu Leu Phe
             20                  25                  30

Ala Leu Ile Phe Leu Val Gly Thr Val Gly Asn Thr Leu Val Leu Ala
             35                  40                  45

Val Leu Leu Arg Gly Gly Gln Ala Val Ser Thr Thr Asn Leu Phe Ile
 50                  55                  60

Leu Asn Leu Gly Val Ala Asp Leu Cys Phe Ile Leu Cys Cys Val Pro
 65                  70                  75                  80

Phe Gln Ala Thr Ile Tyr Thr Leu Asp Gly Trp Val Phe Gly Ser Leu
                 85                  90                  95

Leu Cys Lys Ala Val His Phe Leu Ile Phe Leu Thr Met His Ala Ser
                100                 105                 110

Ser Phe Thr Leu Ala Ala Val Ser Leu Asp Arg Tyr Leu Ala Ile Arg
            115                 120                 125

Tyr Pro Leu His Ser Arg Glu Leu Arg Thr Pro Arg Asn Ala Leu Ala
130                 135                 140

Ala Ile Gly Leu Ile Trp Gly Leu Ser Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Arg Ala Met Asp Ile Cys Thr Phe
            180                 185                 190

Val Phe Ser Tyr Leu Leu Pro Val Leu Val Leu Gly Leu Thr Tyr Ala
            195                 200                 205

Arg Thr Leu Arg Tyr Leu Trp Arg Ala Val Asp Pro Val Ala Ala Gly
210                 215                 220

Ser Gly Ala Arg Arg Ala Lys Arg Lys Val Thr Arg Met Ile Leu Ile
225                 230                 235                 240

Val Ala Ala Leu Phe Cys Leu Cys Trp Met Pro His His Ala Leu Ile
                245                 250                 255

Leu Cys Val Trp Phe Gly Gln Phe Pro Leu Thr Arg Ala Thr Tyr Ala
            260                 265                 270

Leu Arg Ile Leu Ser His Leu Val Ser Tyr Ala Asn Ser Cys Val Asn
            275                 280                 285

Pro Ile Val Tyr Ala Leu Val Ser Lys His Phe Arg Lys Gly Phe Arg
290                 295                 300

Thr Ile Cys Ala Gly Leu Leu Gly Arg Ala Pro Gly Arg Ala Ser Gly
305                 310                 315                 320

Arg Val Cys Ala Ala Ala Arg Gly Thr His Ser Gly Ser Val Leu Glu
                325                 330                 335

Arg Glu Ser Ser Asp Leu Leu His Met Ser Glu Ala Ala Gly Ala Leu
            340                 345                 350
```

```
Arg Pro Cys Pro Gly Ala Ser Gln Pro Cys Ile Leu Glu Pro Cys Pro
        355                 360                 365

Gly Pro Ser Trp Gln Gly Pro Lys Ala Gly Asp Ser Ile Leu Thr Val
    370                 375                 380

Asp Val Ala
385

(2) INFORMATION FOR SEQ ID NO:8:

(i) SEQUENCE CHARACTERISTICS:
        (A) LENGTH: 2234 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCCCTTTCCA CTTTGGTGAT ACCATGAATG GCTCGGACAG CCAGGGGGCG GAGGACTCGA      60

GCCAGGAAGG TGGCGGCGGC TGGCAGCCCG AGGCGGTCCT CGTACCCCTA TTTTTCGCGC     120

TCATCTTCCT CGTGGGCGCT GTGGGCAACG CGCTGGTGCT GGCGGTGCTG CTGCGCGGCG     180

GCCAGGCGGT CAGCACCACG AACCTATTCA TCCTCAACCT GGGTGTGGCC GACCTGTGTT     240

TCATCCTGTG CTGCGTGCCT TTCCAGGCCA CCATCTATAC CCTGGACGAT TGGGTGTTTG     300

GCTCACTGCT CTGCAAGGCC GTTCATTTCC TCATCTTCCT CACTATGCAC GCCAGCAGCT     360

TCACGCTGGC CGCTGTCTCG CTGGACAGGT GAGTGAACAT TCTGTGGTGT CTGAGAACTG     420

GGTACCCAGG TAGGAGCTTG CACTGGAGTC GCCACGCAAG GATCCAGAAG GGATGCGTAG     480

TCGGGGAGAA CACTAAAATT ACAAAGTGGC CCGAGGCCGT GAAACGCAAG GGGAAAGGGG     540

ACTAAGACTC CGTGACTAAG AGTGTCCCTT GATTAAGTCG GTCCTCAGAC CTCGAAGGCT     600

GGAGAAATCG GATTTCTGGG GTCTTTACGT TATTGTTGCT TGAGCTAAAA GTCTCTCAGA     660

AACATTGCAG TACTCAGACC AGAGTTGGCT TGCAAAGTAA CTTGCCAGTA TTCAAATGCT     720

AATTGAGAGC TGCAGAGAGG CATTTGCTTC TTGGCCCCAA GCTCAGCACC TGGAGCGTTG     780

TCCGGCTTTA GGCTTAGGAC TGAGCTGTAC TTTGGATAGA CCCATGCTGA AGTCCAAGGC     840

AGCGGGAGTG AGGGCTCCTA GCGGACGTCT AAAGCCTTCC AGGCCAAGGC TCCCCGCCCG     900

GAGACGCCTG CGGTTTGATG TTCCTTCCCT AGCTAAAGGA CCCAGAAAGA GAAACTTCCA     960

GAATGCTCTG AAGGACTCGT GACTGGAAAA GACACTAGAA ACAGGTCCTG GAAGGATGT    1020

CATTAGTTCC CTGCCCCTTC GCATCACTTG GCCCTTCCCA CAGTAGAGCG GTGAAGAGAG    1080

GCGGAGATCC TCATTCTCTG CTTTCCACTG AGTGCAACAT GTGGGTTCTG AGTCCGCTGG    1140

TGGGACGCAC AAAACTTCAG CTTTCTTCAG GGATTTCCTT GCTCTACCCA AGTCTTCTCC    1200

GGGTTGTCTG TCAGAGAGCC TCAGGCATTA GAGATTTGTC TCCCTCGGTT GTCACAAGAG    1260

GATAATAATC ACTGCCCCCA GAAGTCCTGG CATATTCTAC AACTTTTAGT TTTCGGTGGT    1320

TTGGGGATGC CCTTTCGCGT GGTAGGTCAG TGGCCACATT CTCAGGGTTG GTAATGGTCT    1380

AGCAGTGAAT TAGTGAATCC TTTCGCTTAC CTGTCGTCGT CGTCCCCCCC GCCCCACTGT    1440

CCACTCAGGT ATCTGGCCAT CCGCTACCCG ATGCACTCCC GAGAGTTGCG CACACCTCGA    1500

AACGCGCTGG CGGCCATCGG GCTCATCTGG GGGCTAGCAC TGCTCTTCTC CGGGCCCTAC    1560

CTGAGCTACT ACAGTCAGTC GCAGCTGGCC AATCTGACGG TGTGCCACCC AGCGTGGAGC    1620

GCACCACGAC GTCGCGCCAT GGACCTCTGC ACTTTTGTCT TTAGCTACCT GTTGCCAGTG    1680

CTGGTGCTCA GCCTGACCTA TGCGCGCACC CTGCACTACC TCTGGCGCAC AGTTGACCCA    1740
```

```
GTAGCTGCAG GCTCAGGTTC CCAGCGCGCC AAGCGCAAGG TGACACGGAT GATCGTCATC      1800

GTGGCGGTAC TCTTCTGCCT CTGTTGGATG CCCCACCACG CGCTTATCCT CTGCGTGTGG      1860

TTTGGTCGCT TTCCGCTCAC GCGTGCCACT TACGCCCTGC GCATCCTTTC ACATCTAGTA      1920

TCTTATGCCA ACTCGTGTGT CAACCCCATC GTTTATGCTC TGGTCTCCAA GCATTTCCGC      1980

AAAGGTTTCC GCAAAATCTG CGCGGGCCTG CTACGCCGTG CCCCGAGGAG AGCTTCAGGC      2040

CGAGTGTGCA TCCTGGCGCC TGGAAACCAT AGTGGTGGCA TGCTGGAACC TGAGTCCACA      2100

GACCTGACAC AGGTGAGCGA GGCAGCCGGG CCCCTCGTCC CCGCACCCGC ACTTCCCAAC      2160

TGCACAACCT TGAGTAGAAC CCTCGATCCA GCCTGTTAAA GGACCAAAGG GCATCTAACA      2220

GCTTCTAAGG GCGA                                                         2234
```

(2) INFORMATION FOR SEQ ID NO:9:

(i) SEQUENCE CHARACTERISTICS:
        (A) LENGTH: 371 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met Asn Gly Ser Asp Ser Gln Gly Ala Glu Asp Ser Ser Gln Glu Gly
 1               5                  10                  15

Gly Gly Gly Trp Gln Pro Glu Ala Val Leu Val Pro Leu Phe Phe Ala
            20                  25                  30

Leu Ile Phe Leu Val Gly Ala Val Gly Asn Ala Leu Val Leu Ala Val
        35                  40                  45

Leu Leu Arg Gly Gly Gln Ala Val Ser Thr Thr Asn Leu Phe Ile Leu
    50                  55                  60

Asn Leu Gly Val Ala Asp Leu Cys Phe Ile Leu Cys Cys Val Pro Phe
65                  70                  75                  80

Gln Ala Thr Ile Tyr Thr Leu Asp Asp Trp Val Phe Gly Ser Leu Leu
                85                  90                  95

Cys Lys Ala Val His Phe Leu Ile Phe Leu Thr Met His Ala Ser Ser
            100                 105                 110

Phe Thr Leu Ala Ala Val Ser Leu Asp Arg Tyr Leu Ala Ile Arg Tyr
        115                 120                 125

Pro Met His Ser Arg Glu Leu Arg Thr Pro Arg Asn Ala Leu Ala Ala
    130                 135                 140

Ile Gly Leu Ile Trp Gly Leu Ala Leu Leu Phe Ser Gly Pro Tyr Leu
145                 150                 155                 160

Ser Tyr Tyr Ser Gln Ser Gln Leu Ala Asn Leu Thr Val Cys His Pro
                165                 170                 175

Ala Trp Ser Ala Pro Arg Arg Arg Ala Met Asp Leu Cys Thr Phe Val
            180                 185                 190

Phe Ser Tyr Leu Leu Pro Val Leu Val Leu Ser Leu Thr Tyr Ala Arg
        195                 200                 205

Thr Leu His Tyr Leu Trp Arg Thr Val Asp Pro Val Ala Ala Gly Ser
    210                 215                 220

Gly Ser Gln Arg Ala Lys Arg Lys Val Thr Arg Met Ile Val Ile Val
225                 230                 235                 240

Ala Val Leu Phe Cys Leu Cys Trp Met Pro His His Ala Leu Ile Leu
                245                 250                 255
```

```
Cys Val Trp Phe Gly Arg Phe Pro Leu Thr Arg Ala Thr Tyr Ala Leu
            260                 265                 270

Arg Ile Leu Ser His Leu Val Ser Tyr Ala Asn Ser Cys Val Asn Pro
        275                 280                 285

Ile Val Tyr Ala Leu Val Ser Lys His Phe Arg Lys Gly Phe Arg Lys
        290                 295                 300

Ile Cys Ala Gly Leu Leu Arg Arg Ala Pro Arg Arg Ala Ser Gly Arg
305                 310                 315                 320

Val Cys Ile Leu Ala Pro Gly Asn His Ser Gly Gly Met Leu Glu Pro
                325                 330                 335

Glu Ser Thr Asp Leu Thr Gln Val Ser Glu Ala Ala Gly Pro Leu Val
            340                 345                 350

Pro Ala Pro Ala Leu Pro Asn Cys Thr Thr Leu Ser Arg Thr Leu Asp
            355                 360                 365

Pro Ala Cys
    370

(2) INFORMATION FOR SEQ ID NO:10:

(i) SEQUENCE CHARACTERISTICS:
        (A) LENGTH: 348 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Met Glu Leu Ala Met Val Asn Leu Ser Glu Gly Asn Gly Ser Asp Pro
1               5                   10                  15

Glu Pro Pro Ala Pro Glu Ser Arg Pro Leu Phe Gly Ile Gly Val Glu
            20                  25                  30

Asn Phe Ile Thr Leu Val Val Phe Gly Leu Ile Phe Ala Met Gly Val
            35                  40                  45

Leu Gly Asn Ser Leu Val Ile Thr Val Leu Ala Arg Ser Lys Pro Gly
        50                  55                  60

Lys Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
                85                  90                  95

Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
            115                 120                 125

Met Ser Val Asp Arg Tyr Val Ala Ile Val His Ser Arg Arg Ser Ser
        130                 135                 140

Ser Leu Arg Val Ser Arg Asn Ala Leu Leu Gly Val Gly Phe Ile Trp
145                 150                 155                 160

Ala Leu Ser Ile Ala Met Ala Ser Pro Val Ala Tyr His Gln Arg Leu
                165                 170                 175

Phe His Arg Asp Ser Asn Gln Thr Phe Cys Trp Glu Gln Trp Pro Asn
            180                 185                 190

Lys Leu His Lys Lys Ala Tyr Val Val Cys Thr Phe Val Phe Gly Tyr
        195                 200                 205

Leu Leu Pro Leu Leu Leu Ile Cys Phe Cys Tyr Ala Lys Val Leu Asn
        210                 215                 220
```

His Leu His Lys Lys Leu Lys Asn Met Ser Lys Lys Ser Glu Ala Ser
225                 230                 235                 240

Lys Lys Lys Thr Ala Gln Thr Val Leu Val Val Val Val Phe Gly
            245                 250                 255

Ile Ser Trp Leu Pro His His Val Val His Leu Trp Ala Glu Phe Gly
                260                 265                 270

Ala Phe Pro Leu Thr Pro Ala Ser Phe Phe Arg Ile Thr Ala His
            275                 280                 285

Cys Leu Ala Tyr Ser Asn Ser Ser Val Asn Pro Ile Ile Tyr Ala Phe
        290                 295                 300

Leu Ser Glu Asn Phe Arg Lys Ala Tyr Lys Gln Val Phe Lys Cys His
305                 310                 315                 320

Val Cys Asp Glu Ser Pro Arg Ser Glu Thr Lys Glu Asn Lys Ser Arg
                325                 330                 335

Met Asp Thr Pro Pro Ser Thr Asn Cys Thr His Val
            340                 345

(2) INFORMATION FOR SEQ ID NO:11:

(i) SEQUENCE CHARACTERISTICS:
        (A) LENGTH: 349 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Met Glu Leu Ala Val Gly Asn Leu Ser Glu Gly Asn Ala Ser Cys Pro
1               5                   10                  15

Glu Pro Pro Ala Pro Glu Pro Gly Pro Leu Phe Gly Ile Gly Val Glu
            20                  25                  30

Asn Phe Val Thr Leu Val Val Phe Gly Leu Ile Phe Ala Leu Gly Val
            35                  40                  45

Leu Gly Asn Ser Leu Val Ile Thr Val Leu Ala Arg Ser Lys Pro Gly
    50                  55                  60

Lys Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
                85                  90                  95

Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
            115                 120                 125

Met Ser Val Asp Arg Tyr Val Ala Ile Val His Ser Arg Arg Ser Ser
130                 135                 140

Ser Leu Arg Val Ser Arg Asn Ala Leu Leu Gly Val Gly Cys Ile Trp
145                 150                 155                 160

Ala Leu Ser Ile Ala Met Ala Ser Pro Val Ala Tyr His Gln Gly Leu
            165                 170                 175

Phe His Pro Arg Ala Ser Asn Gln Thr Phe Cys Trp Glu Gln Trp Pro
            180                 185                 190

Asp Pro Arg His Lys Lys Ala Tyr Val Val Cys Thr Phe Val Phe Gly
            195                 200                 205

Tyr Leu Leu Pro Leu Leu Leu Ile Cys Phe Cys Tyr Ala Lys Val Leu
210                 215                 220

```
Asn His Leu His Lys Lys Leu Lys Asn Met Ser Lys Lys Ser Glu Ala
225                 230                 235                 240

Ser Lys Lys Lys Thr Ala Gln Thr Val Leu Val Val Val Val Val Phe
                245                 250                 255

Gly Ile Ser Trp Leu Pro His His Ile Ile His Leu Trp Ala Glu Phe
                260                 265                 270

Gly Val Phe Pro Leu Thr Pro Ala Ser Phe Leu Phe Arg Ile Thr Ala
                275                 280                 285

His Cys Leu Ala Tyr Ser Asn Ser Ser Val Asn Pro Ile Ile Tyr Ala
                290                 295                 300

Phe Leu Ser Glu Asn Phe Arg Lys Ala Tyr Lys Gln Val Phe Lys Cys
305                 310                 315                 320

His Ile Arg Lys Asp Ser His Leu Ser Asp Thr Lys Glu Asn Lys Ser
                325                 330                 335

Arg Ile Asp Thr Pro Pro Ser Thr Asn Cys Thr His Val
                340                 345
```

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...35
        (D) OTHER INFORMATION: PCR primer (xi) SEQUENCE DESCRIPTION: SEQ ID NO:12:

CCGGAATTCG GTACCATGAA CGTCTCGGGC TGCCC     35

(2) INFORMATION FOR SEQ ID NO:13:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...41
        (D) OTHER INFORMATION: PCR primer (xi) SEQUENCE DESCRIPTION: SEQ ID NO:13:

GGTAGCGGAT GGCCAGATAC CTGTCTAGAG AGACGGCGGC C     41

(2) INFORMATION FOR SEQ ID NO:14:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...41

(D) OTHER INFORMATION: PCR primer (xi) SEQUENCE DESCRIPTION: SEQ ID NO:14:

GGCCGCCGTC TCTCTAGACA GGTATCTGGC CATCCGCTAC C                    41

(2) INFORMATION FOR SEQ ID NO:15:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: Other (ix) FEATURE:
         (A) NAME/KEY: Other
         (B) LOCATION: 1...41
         (D) OTHER INFORMATION: PCR primer (xi) SEQUENCE DESCRIPTION: SEQ ID NO:15:

GGCCGCCGTC TCTCTAGACA GGTATCTGGC CATCCGCTAC C                    41

(2) INFORMATION FOR SEQ ID NO:16:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: Other (ix) FEATURE:
         (A) NAME/KEY: Other
         (B) LOCATION: 1...27
         (D) OTHER INFORMATION: PCR primer (xi) SEQUENCE DESCRIPTION: SEQ ID NO:16:

CTGACCGYCA TGRSCATTGA CSGCTAC                                    27

(2) INFORMATION FOR SEQ ID NO:17:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: Other (ix) FEATURE:
         (A) NAME/KEY: Other
         (B) LOCATION: 1...24
         (D) OTHER INFORMATION: PCR primer (xi) SEQUENCE DESCRIPTION: SEQ ID NO:17:

GGGGTTGRSG CAGCTGTTGG CRTA                                       24

(2) INFORMATION FOR SEQ ID NO:18:

(i) SEQUENCE CHARACTERISTICS:
         (A) LENGTH: 1116 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:18:

-continued

| | |
|---|---|
| ATGAATGGCT CCGGCAGCCA GGGCGCGGAG AACACGAGCC AGGAAGGCGG TAGCGGCGGC | 60 |
| TGGCAGCCTG AGGCGGTCCT TGTACCCCTA TTTTTCGCGC TCATCTTCCT CGTGGGCACC | 120 |
| GTGGGCAACG CGCTGGTGCT GGCGGTGCTG CTGCGCGGCG GCCAGGCGGT CAGCACCACC | 180 |
| AACCTGTTCA TCCTCAACCT GGGCGTGGCC GACCTGTGTT TCATCCTGTG CTGCGTGCCT | 240 |
| TTCCAGGCCA CCATCTACAC CCTGGACGAC TGGGTGTTCG GCTCGCTGCT CTGCAAGGCT | 300 |
| GTTCATTTCC TCATCTTTCT CACTATGCAC GCCAGCAGCT TCACGCTGGC CGCCGTCTCC | 360 |
| CTGGACAGGT ATCTGGCCAT CCGCTACCCG CTGCACTCCC GAGAGTTGCG CACACCTCGA | 420 |
| AACGCGCTGG CCGCCATCGG GCTCATCTGG GGCTAGCAC TGCTCTTCTC CGGGCCCTAC | 480 |
| CTGAGCTACT ACCGTCAGTC GCAGCTGGCC AACCTGACGA TATGCCACCC AGCATGGAGC | 540 |
| GCACCTCGAC GTCGAGCCAT GGACCTCTGC ACCTTCGTCT TTAGCTACCT GCTGCCAGTG | 600 |
| CTAGTCCTCA GTCTGACCTA TGCGCGTACC CTGCGCTACC TCTGGCGCAC AGTCGACCCG | 660 |
| GTGACTGCAG GCTCAGGTTC CCAGCGCGCC AAACGCAAGG TGACACGGAT GATCATCATC | 720 |
| GTGGCGGTGC TTTTCTGCCT CTGTTGGATG CCCCACCACG CGCTTATCCT CTGCGTGTGG | 780 |
| TTTGGTCGCT TCCCGCTCAC GCGTGCCACT TACGCGTTGC GCATCCTTTC ACACCTAGTT | 840 |
| TCCTATGCCA ACTCCTGTGT CAACCCCATC GTTTACGCTC TGGTCTCCAA GCATTTCCGT | 900 |
| AAAGGTTTCC GCAAAATCTG CGCGGGCCTG CTGCGCCCTG CCCCGAGGCG AGCTTCGGGC | 960 |
| CGAGTGAGCA TCCTGGCGCC TGGGAACCAT AGTGGCAGCA TGCTGGAACA GGAATCCACA | 1020 |
| GACCTGACAC AGGTGAGCGA GGCAGCCGGG CCCCTTGTCC CACCACCCGC ACTTCCCAAC | 1080 |
| TGCACAGCCT CGAGTAGAAC CCTGGATCCG GCTTGT | 1116 |

(2) INFORMATION FOR SEQ ID NO:19:

(i) SEQUENCE CHARACTERISTICS:
        (A) LENGTH: 1116 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

| | |
|---|---|
| ATGAATGGCT CCGGCAGCCA GGGCGCGGAG AACACGAGCC AGGAAGGCGG TAGCGGCGGC | 60 |
| TGGCAGCCTG AGGCGGTCCT TGTACCCCTA TTTTTCGCGC TCATCTTCTT CGTGGGCACC | 120 |
| GTGGGCAACG CGCTGGTGCT GGCGGTGCTG CTGCGCGGCG GCCAGGCGGT CAGCACCACC | 180 |
| AACCTGTTCA TCCTCAACCT GGGCGTGGCC GACCTGTGTT TCATCCTGTG CTGCGTGCCT | 240 |
| TTCCAGGCCA CCATCTACAC CCTGGACGAC TGGGTGTTCG GCTCGCTGCT CTGCAAGGCT | 300 |
| GTTCATTTCC TCATCTTTCT CACTATGCAC GCCAGCAGCT TCACGCTGGC CGCCGTCTCC | 360 |
| CTGGACAGGT ATCTGGCCAT CCGCTACCCG CTGCACTCCC GAGAGTTGCG CACACCTCGA | 420 |
| AACGCGCTGG CCGCCATCGG GCTCATCTGG GGCTAGCAC TGCTCTTCTC CGGGCCCTAC | 480 |
| CTGAGCTACT ACCGTCAGTC GCAGCTGGCC AACCTGACGA TATGCCACCC AGCATGGAGC | 540 |
| GCACCTCGAC GTCGAGCCAT GGACCTCTGC ACCTTCGTCT TTAGCTACCT GCTGCCAGTG | 600 |
| CTAGTCCTCA GTCTGACCTA TGCGCGTACC CTGCGCTACC TCTGGCGCAC AGTCGACCCG | 660 |
| GTGACTGCAG GCTCAGGTTC CCAGCGCGCC AAACGCAAGG TGACACGGAT GATCATCATC | 720 |
| GTGGCGGTGC TTTTCTGCCT CTGTTGGATG CCCCACCACG CGCTTATCCT CTGCGTGTGG | 780 |
| TTTGGTCGCT TCCCGCTCAC GCGTGCCACT TACGCGTTGC GCATCCTTTC ACACCTAGTT | 840 |

```
TCCTATGCCA ACTCCTGTGT CAACCCCATC GTTTACGCTC TGGTCTCCAA GCATTTCCGT    900

AAAGGTTTCC GCAAAATCTG CGCGGGCCTG CTGCGCCCTG CCCCGAGGCG AGCTTCGGGC    960

CGAGTGAGCA TCCTGGCGCC TGGGAACCAT AGTGGCAGCA TGCTGAACA GGAATCCACA    1020

GACCTGACAC AGGTGAGCGA GGCAGCCGGG CCCCTTGTCC CACCACCCGC ACTTCCCAAC   1080

TGCACAGCCT CGAGTAGAAC CCTGGATCCG GCTTGT                             1116
```

(2) INFORMATION FOR SEQ ID NO:20:

(i) SEQUENCE CHARACTERISTICS:
        (A) LENGTH: 372 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

```
Met Asn Gly Ser Gly Ser Gln Gly Ala Glu Asn Thr Ser Gln Glu Gly
 1               5                  10                  15

Gly Ser Gly Gly Trp Gln Pro Glu Ala Val Leu Val Pro Leu Phe Phe
            20                  25                  30

Ala Leu Ile Phe Phe Val Gly Thr Val Gly Asn Ala Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Asp Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ala Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Arg Ala Met Asp Leu Cys Thr Phe
            180                 185                 190

Val Phe Ser Tyr Leu Leu Pro Val Leu Val Leu Ser Leu Thr Tyr Ala
        195                 200                 205

Arg Thr Leu Arg Tyr Leu Trp Arg Thr Val Asp Pro Val Thr Ala Gly
    210                 215                 220

Ser Gly Ser Gln Arg Ala Lys Arg Lys Val Thr Arg Met Ile Ile Ile
225                 230                 235                 240

Val Ala Val Leu Phe Cys Leu Cys Trp Met Pro His His Ala Leu Ile
                245                 250                 255

Leu Cys Val Trp Phe Gly Arg Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300
```

-continued

```
Lys Ile Cys Ala Gly Leu Leu Arg Pro Ala Pro Arg Arg Ala Ser Gly
305                 310                 315                 320

Arg Val Ser Ile Leu Ala Pro Gly Asn His Ser Gly Ser Met Leu Glu
                325                 330                 335

Gln Glu Ser Thr Asp Leu Thr Gln Val Ser Glu Ala Ala Gly Pro Leu
            340                 345                 350

Val Pro Pro Pro Ala Leu Pro Asn Cys Thr Ala Ser Ser Arg Thr Leu
        355                 360                 365

Asp Pro Ala Cys
    370
```

NUCLEIC ACID ENCODING RAT GALANIN RECEPTOR (GALR2)

CROSS-REFERENCE TO RELATED APPLICATIONS

The present application claims priority to application Ser. No. 60/033,851, filed Dec. 27, 1996.

FIELD OF THE INVENTION

This invention relates to a novel galanin receptor, designated GALR2, to nucleotides encoding it, and to assays which use it.

BACKGROUND OF THE INVENTION

Although first isolated from porcine intestine, galanin is widely distributed in the central and peripheral nervous system. Galanin in most species is a 29 amino acid peptide with an amidated carboxyl terminus. Human galanin is unique in that it is longer, 30 amino acids, and is not amidated. There is strong conservation of the galanin sequence with the amino terminal fifteen residues being absolutely conserved in all species. Galanin immunoreactivity and binding is abundant in the hypothalamus, the locus coeruleus, the hippocampus and the anterior pituitary, as well as regions of the spinal cord, the pancreas and the gastrointestinal tract.

Like neuropeptide Y (NPY), injection of galanin into the paraventricular nucleus (PVN) of the hypothalamus produces a dose-dependent increase in feeding in satiated rats. While galanin, like norepinephrine, enhances carbohydrate ingestion, some studies have shown that it profoundly increases fat intake. It has been suggested that galanin shifts macronutrient preference from carbohydrate to fat. The same injections that increase feeding reduce energy expenditure and inhibit insulin secretion. There is enhanced galanin expression in the hypothalamus of genetically obese rats compared with their lean littermate controls. Injection of peptide receptor antagonists into the PVN blocks the galanin-specific induction of increased fat intake. Specific galanin antisense oligonucleotides when injected into the PVN produce a specific decrease in galanin expression associated with a decrease in fat ingestion and total caloric intake while hardly affecting either protein or carbohydrate intake. Thus galanin appears to be one potential neurochemical marker related to the behavior of fat ingestion.

Galanin inhibits cholinergic function and impairs working memory in rats. Lesions that destroy cholinergic neurons result in deficits in spatial learning tasks. While locally administered acetylcholine (ACh) reverses some of this deficit, galanin blocks this ACh-mediated improvement. Evidence from autopsy samples from Alzheimer's disease-afflicted brains suggests an increased galinergic innervation of the nucleus basilis. Thus, if galinergic overactivity contributes to the decline in cognitive performance in Alzheimer's disease, galanin antagonists may be therapeutically useful in alleviating cognitive impairment.

In the rat, administration of galanin intracerebroventricularly, subcutaneously or intravenously increases plasma growth hormone. Infusion of human galanin into healthy subjects also increases plasma growth hormone and potently enhances the growth hormone response to GHRH.

Galanin levels are particularly high in dorsal root ganglia. Sciatic nerve resection dramatically up-regulates galanin peptide and mRNA levels. Chronic administration of galanin receptor antagonists (M35, M15) after axotomy results in a marked increase in self mutilation behavior in rats, generally considered to be a response to pain. Application of antisense oligonucleotides specific for galanin to the proximal end of a transected sciatic nerve suppressed the increase in galanin peptide levels with a parallel increase in autotomy. Galanin injected intrathecally acts synergistically with morphine to produce analgesia, this antinociceptive effect of morphine is blocked by galanin receptor antagonists. Thus, galanin agonists may have some utility in relieving neural pain.

The actions of galanin are mediated by high affinity galanin receptors that are coupled by pertussis toxin sensitive $G_i/G_o$ proteins to inhibition of adenylate cyclase activity, closure of L-type $Ca^{++}$ channels and opening of ATP-sensitive $K^+$ channels. Specific binding of $^{125}I$-galanin (Kd approximately 1 nM) has been demonstrated in areas paralleling localization of galanin immunoreactivity: hypothalamus, ventral hippocampus, basal forebrain, spinal cord, pancreas and pituitary. In most tissues the amino terminus (GAL 1-15) is sufficient for high affinity binding and agonist activity.

Recently, a galanin receptor cDNA was isolated by expression cloning from a human Bowes melanoma cell line. (Habert-Ortoli, et al. 1994. Proc. Nat. Acad. Sci,, USA 91: 9780–9783). This receptor, GALR1, is expressed in human fetal brain and small intestine, but little else is known of its distribution. Gal(1-16) is at least 1000 times more active than pGAL(3-29) as an inhibitor of $^{125}I$-porcine galanin binding to this receptor transiently expressed in COS cells. It remains to be determined whether this receptor subtype represents the hypothalamic receptor that mediates the galanin specific feeding behavior.

It would be desirable to identify further galanin receptors so that they can be used to further characterize this biological system and to identify galanin receptor subtype selective agonists and antagonists.

SUMMARY OF THE INVENTION

This invention relates to a novel galanin receptor, designated GALR2, substantially free from associated proteins, and to GALR2-like receptors which are at least about 40% homologous and which have substantially the same biological activity. In preferred embodiments of this invention, the GALR2-like receptors are at least about 60%, and more preferably at least about 75%, and even more preferably at least about 85% homologous to a GALR2 receptor. This invention also relates specifically to rat, human and mouse GALR2, substantially free from associated proteins, and to receptors which are at least about 50% homologous and which have substantially the same biological activity.

Another aspect of this invention are primate and non-primate GALR2 proteins which are encoded by substantially the same nucleic acid sequences, but which have undergone changes in splicing or other RNA processing-derived modifications or mutagenesis-induced changes, so that the expressed protein has a homologous, but different amino acid sequence from the native forms. These variant forms may have different and/or additional functions in human and animal physiology or in vitro in cell based assays.

A further aspect of this invention are nucleic acids which encode a galanin receptor or a functional equivalent from rat, human, mouse, swine, or other species. These nucleic acids may be free from associated nucleic adds, or they may be isolated or purified. The nucleic acids which encode a receptor of this invention may be any type of nucleic acid. Preferred forms are DNAs, including genomic and cDNA, although this invention specifically includes RNAs as well. Nucleic acid constructs may also contain regions which control transcription and translation such as one or more promoter regions, termination regions, and if desired enhancer regions. The nucleic acids may be inserted into any known vector including plasmids, and used to transfect suitable host cells using techniques generally available to one of ordinary skill in the art.

Another aspect of this invention are vectors comprising nucleic acids which encode GALR2, and host cells which contain these vectors. Still another aspect of this invention is a method of making GALR2 comprising introducing a vector comprising nucleic acids encoding GALR2 into a host cell under culturing conditions.

Yet another aspect of this invention are assays for GALR2 ligands which utilize the receptors and/or nucleic acids of this invention. Preferred assays of this embodiment compare the binding of the putative GALR2 ligand to the binding of galanin to GALR2.

BRIEF DESCRIPTION OF THE DRAWINGS

FIGS. 1A and 1B provide the nucleic acid sequence of rat GALR2 (clone 27A) containing 5' and 3' untranslated regions (SEQ ID NO:1).

FIGS. 2A and 2B provide the nucleic acid sequence of GALR2 (clone 27A) from initiator Met to polyadenylation (positions 296–2,200 of SEQ ID NO: 1).

FIG. 4 is the deduced amino acid sequence of GALR2 (clone 27A) (SEQ ID NO: 2).

FIGS. 5A and 5B provide a comparison (PileUp alignment) of amino acid sequences for rat GALR1 (SEQ ID. NO: 3) and rat GALR2 (SEQ ID. NO:2).

FIG. 6 is the nucleic acid sequence of the cDNA probe used to isolate GALR2 (SEQ ID NO:4).

FIGS. 7A and 7B provide the DNA sequence of human GALR2 gene (SEQ ID NO:5).

FIG. 8 is the DNA sequence (open reading frame only) of human GALR2 gene (SEQ ID NO:6).

FIGS. 9A and 9B provide the deduced amino acid sequence of human GALR2 (SEQ ID NO:7).

FIG. 10 demonstrates the pharmacology of human and rat GALR2.

FIG. 12 is the DNA sequence of mouse GALR2 gene (SEQ ID. NO:8).

FIG. 13 is the amino acid sequence for mouse GALR2 gene (SEQ ID NO:9).

FIGS. 14A and 14B, 14C and 14D provide a comparison of human, rat and mouse GALR1 and GALR2 protein sequences showing strong sequence conservation among members of the GALR gene family mGALR1 is SEQ ID NO: 10; rGALR1 is SEQ ID NO: 3; hGALR1 is SEQ ID NO: 11; mGALR2 is SEQ ID NO: 9; rGALR2 is SEQ ID NO: 2; hGALR2 is SEQ ID NO: 7.

FIG. 15 is the RNA expression profile of human GALR2.

DETAILED DESCRIPTION OF THE INVENTION

Figure 3:
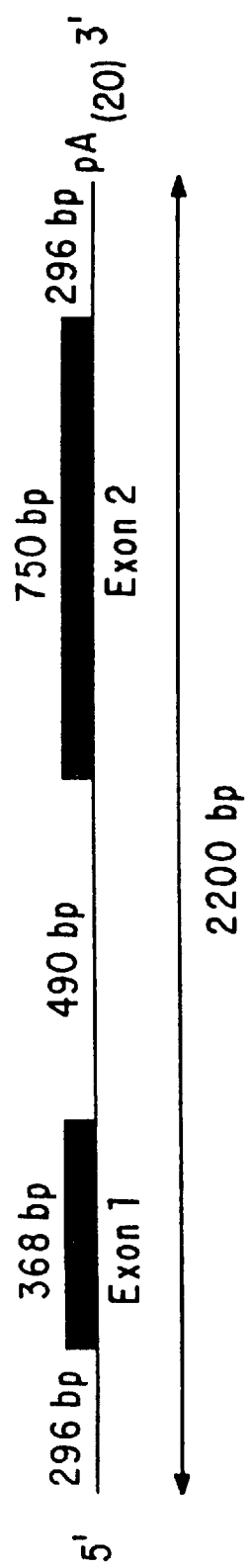
FIGS. 3A and 3B provide a schematic representation of GALR2 (clone 27A) and the nucleic acid (positions 296–1, 904 of SEQ ID NO: 1). and deduced amino acid (SEQ ID NO:2) sequence of GALR2 (clone 27A).

As used throughout the specification and claims, the following definitions apply:

"Substantially free from associated proteins" means that the receptor is at least about 90%, and preferably at least about 95% free from other cell membrane proteins which are normally found in a living mammalian cell which expresses a galanin receptor.

"Substantially free from associated nucleic acids" means that the nucleic acid is at least about 90%, and preferably at least about 95%, free from other nucleic acids which are normally found in a living mammalian cell which naturally expresses a galanin receptor gene.

"Substantially the same biological activity" means that the receptor-galanin binding constant is within 5-fold of the binding constant of GALR2 and galanin, and preferably within 2-fold of the binding constant of GALR2 and galanin.

"Stringent post-hybridizational washing conditions" means 0.1×standard saline citrate (SSC) at 65° C.

"Standard post-hybridizational washing conditions" means 6×SSC at 55° C.

"Relaxed post-hybridizational washing conditions" means 6×SSC at 30° C., or 1 to 2×SSC at 55° C.

"Functional equivalent" means that a receptor which does not have the exact same amino acid sequence of a naturally occurring GALR2 protein due to alternative splicing, deletions, mutations, or additions, but retains at least 1%, preferably 10%, and more preferably 25% of the biological activity of the naturally occurring receptor. Such derivatives will have a significant homology with a natural GALR2 and can be detected by reduced stringency hybridization with a DNA sequence obtained from a GALR2. The nucleic acid encoding a functional equivalent has at least about 60% homology at the nucleotide level to a naturally occurring receptor nucleic acid.

It has been found, in accordance with this invention, that there is a second galanin receptor, which is designated GALR2. The rat, human and mouse GALR2 sequences are given in FIGS. 4, 9 and 13, respectively, and are referenced in the Examples; however it is to be understood that this invention specifically includes GALR2 without regard to the species and, in particular, specifically includes rodent (including rat and mouse), rhesus, swine, chicken, cow and human. The galanin 2 receptors are highly conserved throughout species, and one of ordinary skill in the art, given the rat, human and/or mouse sequences presented herein, can easily design probes to obtain the GALR2 from other species.

GALR2 proteins contain various functional domains, including one or more domains which anchor the receptor in the cell membrane, and at least one ligand binding domain. As with many receptor proteins, it is possible to modify many of the amino acids, particularly those which are not found in the ligand binding domain, and still retain at least a percentage of the biological activity of the original receptor. Thus this invention specifically includes modified functionally equivalent GALR2s which have deleted, truncated, or mutated N-terminal portions. This invention also specifically includes modified functionally equivalent GALR2s which contain modifications and/or deletions in other domains, which are not accompanied by a loss of functional activity.

Additionally, it is possible to modify other functional domains such as those that interact with second messenger effector systems, by altering binding specificity and/or selectivity. Such functionally equivalent mutant receptors are also within the scope of this invention.

The proteins of this invention were found to have structural features which are typical of the 7-transmembrane domain (TM) containing G-protein linked receptor superfamily (GPC-R's or 7-TM receptors). Thus GALR2 proteins make up new members of the GPC-R family of receptors. The intact GALR2 of this invention was found to have the general features of GPC-R's, including seven transmembrane regions, three intra- and extracellular loops, and the GPC-R protein signature sequence. The TM domains and GPC-R protein signature sequence are noted in the protein sequences of the GALR2. Not all regions are required for functioning, and therefore this invention also comprises functional receptors which lack one or more non-essential domains.

Determination of the nucleotide sequence indicated that the GALR2 belongs to the intron-containing class of GPC-R's. Clone 27A, a precursor mRNA terminating in a poly (A) tract, encodes a 1119 bp open reading frame divided into two exons by a single intron of approximately 500 bp (FIG. 4). Exon 1 encodes the N-terminal extracellular domain through predicted TM-3, while exon 2 encodes the second predicted extracellular loop through the C-terminal intracellular domain. A perfectly conserved splice donor site (G/gt) is found at nucleotide 368 which coincides with the second residue of the G protein-coupled receptor signature aromatic triplet, (D,E) RY.

Removal of the intron indicates that clone 27A encodes a full-length rat galanin receptor polypeptide of 372-amino acids with 7 predicted TM domains, as underlined in FIG. 4. Searches of nucleic acid and protein sequence databases revealed that the open reading frame sequence is unique and most closely related to rat galanin 1 receptor (GALR1) with 55% nucleic acid and 38% protein sequence identity. An alignment of the protein sequences for rat GALR1 and GALR2 is given in FIG. 5. Several conserved features ascribed to GPC-R's were also identified in the rat GALR2: the signature aromatic triplet sequence (Glu-Arg-Tyr) adjacent to TM-3, Cys-98 and Cys-153 in the first two extracellular loops capable of disulfide bonding, putative amino-terminal N-glycosylation sites (Asn-Xaa-Ser/Thr), phosphorylation sites in the carboxyl-terminus and the third cytoplasmic loop, and conserved proline residues in TM-4, 5, 6 and 7.

A second cDNA clone was isolated, termed clone 16.6, which does not contain an intron and is therefore a contiguous cDNA containing the complete open reading frame of GALR2. Like clone 27A, Clone 16.6 contains a 5' untranslated region of approximately 500 bp, a contiguous GALR2 open reading frame encoding 7-TM domains (1119 bp), a 3' untranslated region of about 320 bp, and a poly (A) tract. The open reading frame sequence is identical for clones 27A (SEQ ID NO:18) and 16.6 (SEQ ID NO:19) except for nucleotide 109 of the open reading frame (located in predicted TM-1). Clone 27A contains a C while Clone 16.6 contains a T in position 109. Thus, amino acid 37 of the GALR2 protein is phenylalanine in Clone 16.6 (SEQ ID NO:20) and leucine in Clone 27A. Both the DNAs of clones 27A and Clone 16.6 form aspects of this invention, as do their respective proteins.

The human GALR2 protein bears strong sequence identity and similarity to the rat GALR2 ortholog. One notable difference between the human and rat forms is the presence of an additional 15 amino acids in the C-terminal intracellular domain of human GALR2. The mouse protein sequence, as well, bears very strong identity and similarity with the GALR gene family.

This invention also relates to truncated forms of GALR2, particularly those which encompass the extracellular portion of the receptor, but lack the intracellular signaling portion of the receptor, and to nucleic acids encoding these truncated forms. Such truncated receptors are useful in various binding assays. Thus this invention specifically includes modified functionally equivalent GALR2s which have deleted, truncated, or mutated N-terminal portions. This invention also specifically includes modified functionally equivalent GALR2s including receptor chimeras which contain modifications and/or deletions in other domains, which are not accompanied by a loss of functional activity.

Additionally, it is possible to modify other functional domains such as those that interact with second messenger effector systems, by altering binding specificity and/or selectivity. Such functionally equivalent mutant receptors are also within the scope of this invention.

Assays which make up further aspects of this invention include binding assays (competition for $^{125}$I-galanin binding), coupling assays (including galanin-mediated inhibition of forskolin-stimulated adenylate cyclase in cells expressing galanin receptors), measurement of galanin-stimulated calcium release in cells expressing galanin receptors (such as aequorin assays), stimulation of inward rectifying potassium channels (GIRK channels, measured by voltage changes) in cells expressing galanin receptors, and measurement of pH changes upon galanin stimulation of cells expressing galanin receptors as measured with a microphysiometer.

Host cells may be cultured under suitable conditions to produce GALR2. An expression vector containing DNA encoding the receptor may be used for expression of receptor in a recombinant host cell. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to Drosophila, Spodoptera, and silkworm derived cell lines. Cell lines derived from mammalian species which are suitable and which are commercially available include, but are not limited to, L cells L-M(TK$^-$) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The specificity of binding of compounds showing affinity for the receptor is shown by measuring the affinity of the compounds for cells transfected with the cloned receptor or for membranes from these cells. Expression of the cloned receptor and screening for compounds that inhibit the binding of radiolabeled ligand to these cells provides a rational way for rapid selection of compounds with high affinity for the receptor. These compounds identified by the above assays may be agonists or antagonists of the receptor and may be peptides, proteins, or non-proteinaceous organic molecules. Alternatively, functional assays of the receptor may be used to screen for compounds which affect the activity of the receptor. Such functional assays range from ex vivo muscle contraction assays to assays which determine second messenger levels in cells expressing the receptor. The second messenger assays include, but are not limited to, assays to measure cyclic AMP or calcium levels or assays to measure adenyl cyclase activity. These compounds identified by the above assays may be agonists, antagonists, suppressors, or inducers of the receptor. The functional activity of these compounds is best assessed by using the receptor either natively expressed in tissues or cloned and exogenously expressed.

Using the assays of this invention, galanin agonists and antagonists may be identified. A galanin agonist is a compound which binds to the GALR2, such as a galanin mimetic, and produces a cellular response which is at least about equivalent to that of galanin, and which may be greater than that of galanin. Such compounds would be useful in situations where galanin insufficiency causes anorexia, or for treatment of pain.

Also using this embodiment of the assay, galanin antagonists may be identified. A galanin antagonist is a compound which can bind to the GALR2, but produces a lesser response than that of native galanin. Such compounds would be useful in the treatment of obesity.

One assay of this invention is a method of identifying a compound which modulates GALR2 receptor comprising: a) culturing cells expressing the GALR2 receptor in the presence of the compound and b) measuring GALR2 receptor activity or second messenger activity. If desired, the determined activity can be compared to a standard, such as that measured using galanin as the compound. In preferred embodiments, the cells are transformed and express the GALR2 receptor.

The consultant cDNA clone (or shorter portions of, for instance, only 15 nucleotides long) may be used to probe libraries under hybridization conditions to find other receptors which are similar enough so that the nucleic acids can hybridize, and is particularly useful for screening libraries from other species. In this step, one of ordinary skill in the art will appreciate that the hybridization conditions can vary from very stringent to relaxed. Proper temperature, salt concentrations, and buffers are well known.

The following non-limiting Examples are presented to better illustrate the invention.

EXAMPLE 1

A cDNA library from rat hypothalamus was constructed in the plasmid-based mammalian vector pcDNA-3 (InVitrogen, San Diego, Calif.). Total RNA was isolated from freshly-dissected rat hypothalami (flash-frozen in liquid nitrogen) using the RNagents total RNA isolation kit (Promega Biotech, Madison, Wis.) with a yield of approximately 0.5 mg from 1 g (wet weight) of hypothalamic tissue. Poly (A)$^+$ mRNA was selected using the Poly A tract mRNA Isolation System III (Promega Biotech) with a yield of approximately 6 µg from 0.5 µg total RNA. 3 µg of poly (A)$^+$ was then utilized as a template for cDNA synthesis using a kit (Choice Superscript, Life Technologies, Gaithersberg, Md.) with both random hexamer and oligo (dT)-Not I priming. The double-stranded cDNA was adapted for insertion into the BstXI site of pcDNA-3 using EcoRI/BstXI adapters and transformed by electroporation into the *E. coli* strain HB101. The resulting library contained approximately 750,000 primary transformants with 90% of the clones containing inserts (average size 1–2 kb). The library (approximately 700,000 cfu) was plated onto LB plates containing ampicillin and chloramphenicol and probed with an approximately 280 bp PCR fragment (SEQ ID NO:4). Hybridization was conducted at 32° C. for 18 hrs. in 5×SSPE buffer containing 50% formamide, 4×Denhardt's solution, 0.1% SDS, 10% dextran sulfate, 30 µg/ml sheared salmon-sperm DNA with 2×10$^6$ cpm/ml of $^{32}$P-labeled probe. The probe was radiolabeled by random-priming with [α]$^{32}$P-dCTP to a specific activity of greater than 10$^9$ dpm/µg. The filters were then washed in 1×SSC, 0.1% SDS at 55° C. and exposed to film (Kodak X-omat) for 48 hrs. Two independent positive clones were identified (clones 27A and 16.6) and subjected to further analysis.

EXAMPLE 2
Sequence Analysis of GALR2

DNA was prepared from overnight cultures using the Wizard DNA Purification System (Promega Corp., Madison, Wis.) and subjected to automated sequence analysis using the PRISM Dye Deoxy terminator cycle sequencing kit (Applied Biosystems, Foster City, Calif.) on an ABI 377 instrument. Initial sequencing primers were complementary to the T7 and SP6 promoter sites in pcDNA-3, additional primers were made complementary to the insert DNA. Database searches (Genbank, EMBL, Swiss-Prot, PIR, dEST, Prosite, dbGPCR), sequence alignments, and analysis of the galanin receptor nucleotide and protein sequences were carried out using the GCG Sequence Analysis Software Package (Madison, Wis.; pileup, peptide structure and motif programs), FASTA and BLAST search programs, and the PC/Gene software suite from Intelligenetics (San Francisco, Calif.; protein analysis programs).

EXAMPLE 3
Construction of a Vector for Expression of GALR2

Five µg of the mammalian expression vector pCI.neo (Promega Biotech, Madison, Wis.) was digested with 20 units of EcoRI for 2 hours at 37° C. The digest was then treated with calf intestinal phosphatase and then electrophoresed on 1% Seaplaque gel in 1×TAE buffer and the band corresponding to linearized vector was cut out. DNA was recovered from the slice after melting at 65° C. using the Promega Wizard PCR system (Promega Biotech). DNA was quantitated by electrophoresis with standards on a 1% TBE gel. 100 ng of the 2200 bp EcoRI insert (including the intron) from pcDNA-3/27A was ligated to 50 ng of the vector pCI.neo in a 10 ml reaction at room temperature for 1 hour. 1 µl of this ligation mixture was used to transform 50 µl competent DH5a cells (Life Technologies). Clones in the correct orientation were selected following a digest with BamHI. Transfection-quality DNA was then prepared using the Qiagen Maxi protocol (Qiagen, Chatsworth, Calif.). Mammalian COS-7 cells were transfected by electroporation. COS-7 cells (1×10$^7$) were suspended in 0.85 ml of Ringers' buffer and 15 mg of the pCI.neo/27A clone was added to a 0.4 mm electroporation cuvette (Bio-Rad, Hercules, Calif.). Current was applied (960 µF, 260 V) using a Bio-Rad Electroporator device and the cells were transferred to a T-180 flask (Corning). Expression was allowed to proceed for 72 hrs.

EXAMPLE 4
Pharmacology of GALR2

Membranes were prepared from transfected cells following dissociation in enzyme-free dissociation solution (Specialty Media, Lavallette, N.J.) by disruption in a Dounce homogenizer in ice-cold membrane buffer (10 mM Tris, pH 7.4, 10 mM PMSF, 10 µM phosphoramidon, and 40 µg/ml bacitracin). After a low speed (1100×g for 10 min. at 4° C.) and a high speed centrifugation (38,700×g for 15 min. at 4° C.), membranes were resuspended in buffer and protein concentration determined (Bio-Rad assay kit). Binding of $^{125}$I-human galanin (specific activity of 2200 Ci/mmol, DuPont NEN) was measured in membranes using a buffer of 25 mM Tris pH 7.4, 0.5% BSA, 2 mM MgCl$_2$, 40 µg/ml bacitracin, 4 µg/ml phosphoramidon, and 10 µM leupeptin in a total volume of 250 µl. 70 pM $^{125}$I-human galanin was used. Reactions were initiated by the addition of membranes and the incubation was allowed to proceed at room temperature for 1 hour. Nonspecific binding was defined as the amount of radioactivity remaining bound in the presence of 1 μM cold galanin. In competition studies various concentrations of peptides (hGal, pGal, hGal(1-16), rGAL(2-29), rGAL(3-29), hGal (1-19) or chimeric peptides (C7, M15, M40, M35) were included along with $^{125}$I-hGal (70 pmol). Incubations were terminated by rapid filtration through GF/C filters which had been presoaked with 0.1% polyethylamine using a TOMTEC (Orange, Conn.) cell harvester. The results were analyzed using the Prism software package (GraphPad, San Diego, Calif.). Shown in the table below is the ligand binding profiles of both rat GALR1 and rat GALR2 proteins (clone 27A shown; clone 16.6 gave similar results). The $K_D$ for binding of $^{125}$I-labeled human galanin against rat GALR2 was 0.2 nM.

|  | IC50 (nM) | |
| --- | --- | --- |
|  | rat GALR1 | rat GALR2 (clone 27A) |
| pig Galanin | 0.06 | 0.46 |
| human Galanin | 0.07 ± 0.01 | 1.3 ± 0.5 |
| rat Gal (2-29) | 7.2 | 2.9 ± 1.3 |
| rat Gal (3-29) | >1000 | >1000 |
| human Gal (1-19) | 0.86 |  |
| pig Gal (1-16) | 0.27 ± 0.18 | 3.0 |
| galantide (M15) | 1.0 ± 1.1 | 28 ± 3.5 |
| C7 | 4.9 ± 3 | 23 ± 13 |
| M40 | 0.01 | 1.9 ± 0.14 |
| M35 | 0.9 ± 0.6 | 0.43 ± 0.18 |

EXAMPLE 5

Expression of Rat GALR2

Figure 16:
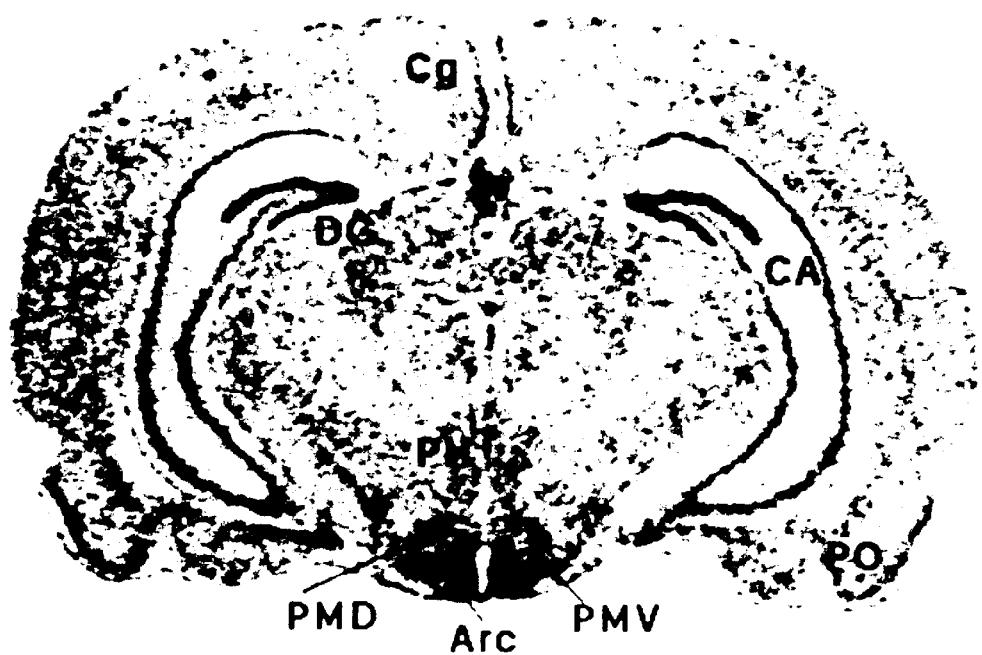
FIG. 16 illustrates the expression of rat GALR2 in the brain.

In situ hybidization was conducted to map the distribution of GALR2 mRNA in rat brain using a $^{32}$P-labeled GALR2 ORF fragment as a hybridization probe; see O'Dowd, B. F. et al. 1995 Genomics 28:84–91. Specific hybridization was detected in a number of brain nuclei and regions, most notably supra-, pre-(PMD/PMV), med- and lateral mammillary nuclei, the dendate gyrus (DG), cingulate gyrus (CG), posterior hypothalamic (PH), supraoptic and arcuate nuclei (Arc) as shown in FIG. 16. Both frontal and parietal cortical regions were also labeled.

Clone Isolation of Human GALR2: Cloning of Partial GalR2 Gene by Degenerate PCR

Human genomic DNA was amplified by PCR using degenerate oligonucleotides designed based on the sequences encoding transmembranes (TM) regions TM3 (P1: 5' CTG ACC GYC ATG RSC ATT GAC SGC TAC, SEQ ID NO:16, wherein Y=C or T, R=A or G, S=C or G) and TM7 (P2: 5'-GGG GTT GRS GCA GCT GTT GGC RTA, SEQ ID NO:17) of somatostatin receptors and the receptor encoded by the somatostatin-related gene, SLC-1. The PCR conditions were as follows: denaturation at 95° C. for 1 min, annealing at either 55° C., 45° C., or 38° C. for 1 min and extension at 72° C. for 2.5 min for 30 cycles, followed by a 7 min extension at 72° C. The resultant PCR products were phenol/chloroform extracted, precipitated with ethanol, phosphorylated with T4 polynucleotide kinase, and blunt-ended with Klenow enzyme. Subsequently, they were electrophoresed on a 0.5% low-melting point agarose and a fragment of the expected size was subcloned into the EcoRV site of pBluescript SK(–) (Stratagene, La Jolla, Calif.). Colonies were selected, plasmid DNA was purified, and the inserts sequenced.

EXAMPLE 6

Gene Sequence and Structure: Cloning and Sequencing of Human GalR2 Genomic DNA

Figure 14A:
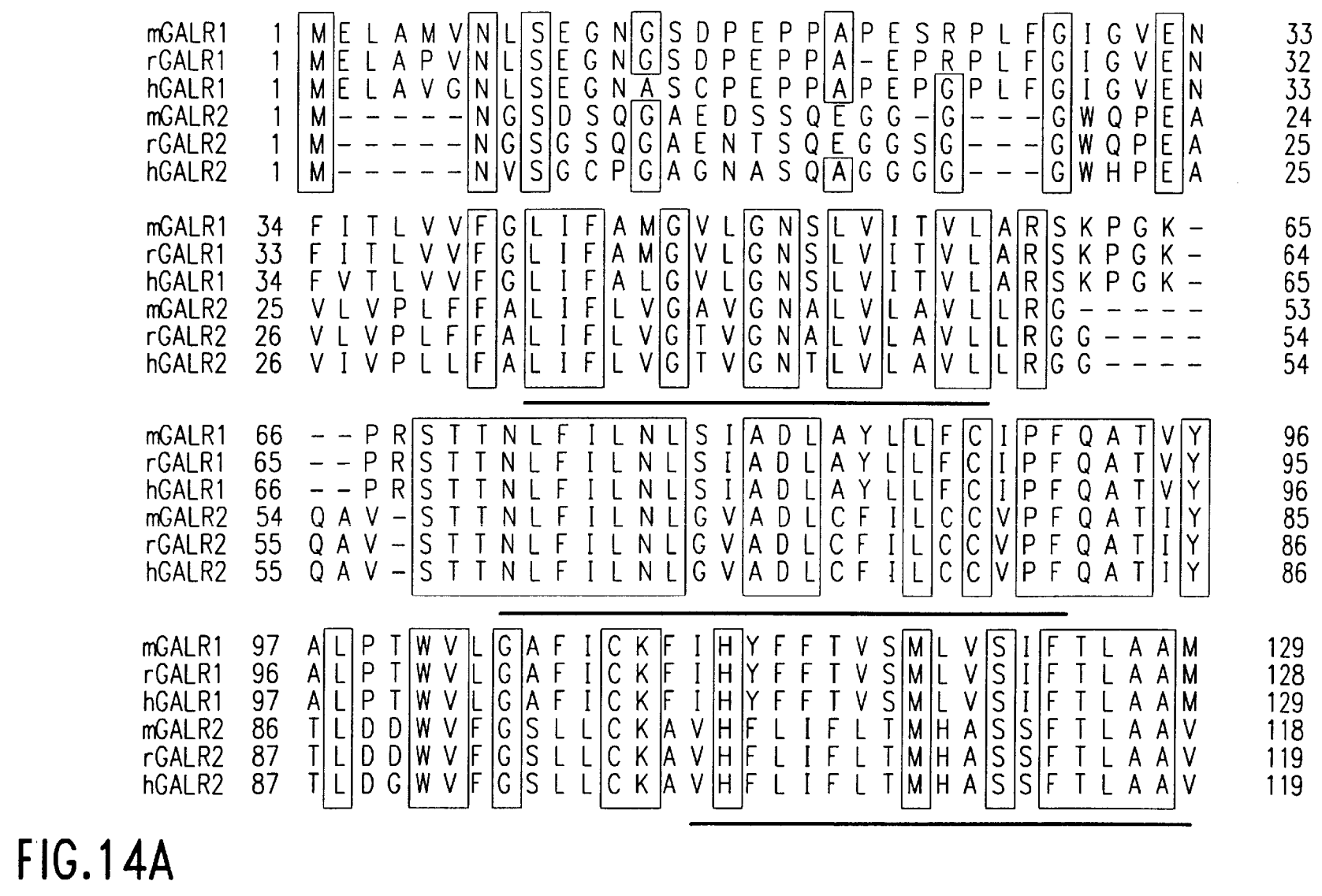
Figure 14C:
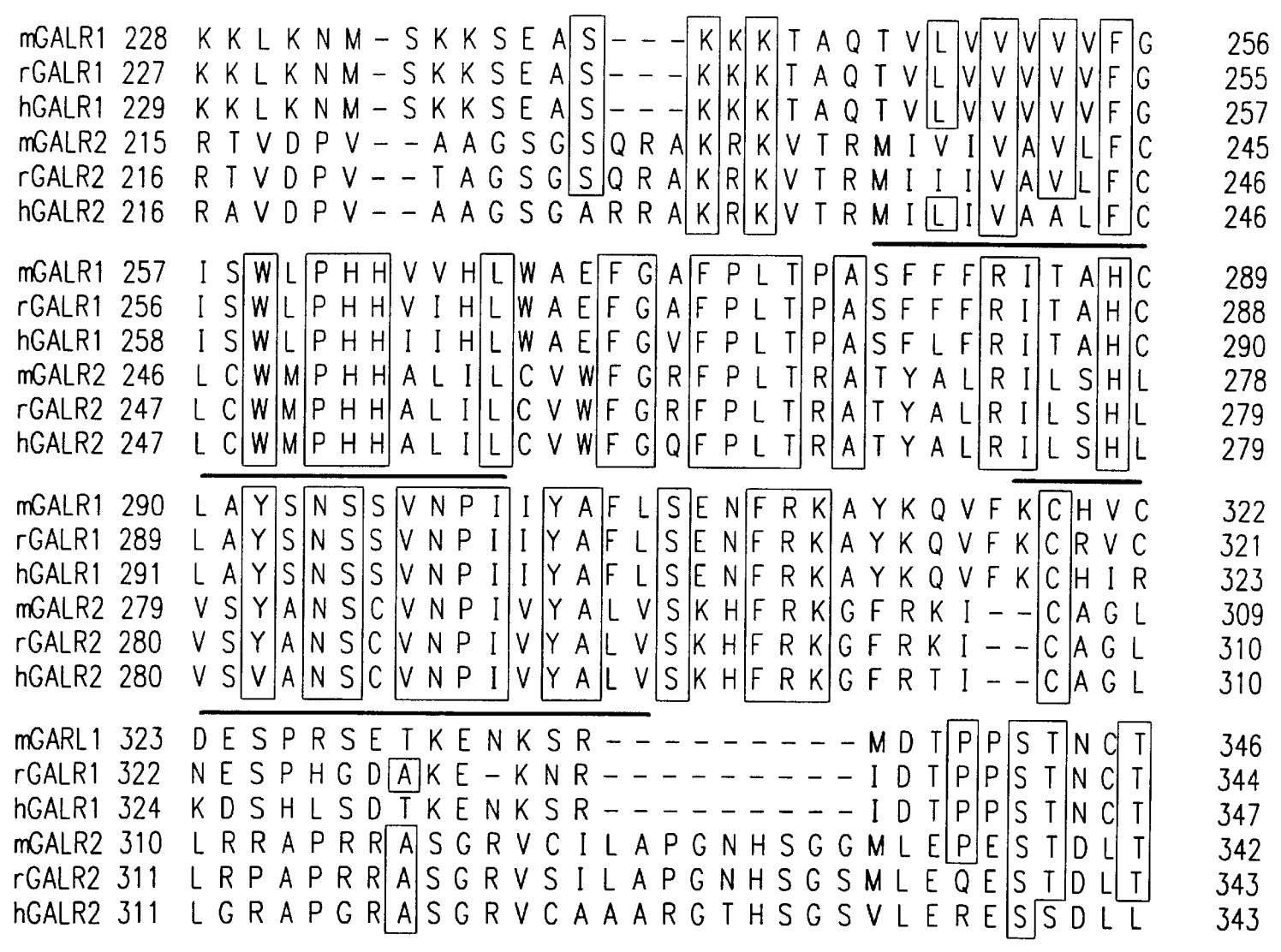

DNA fragments radiolabelled with [32P]dCTP by nick translation (Amersham) were used as a probe to screen a EMBL3 SP6/T7 human genomic library (Clontech, Palo Alto, Calif.). Positive phage clones were plaque purified, DNA was prepared, restriction enzyme digested, electrophoresed on an agarose gel, transferred to nylon membrane, and hybridized with the same probe used to screen the library, as described by Marchese et al, 1994 [Genomics 23, 609–618]. Positive phage were subcloned by digesting phage DNA, and subcloning the resultant fragment into the pBluescript vector. The DNA sequence of the done was determined using standard methods on an ABI 372 automated sequencer (Perkin-Elmer-Applied Biosystems, Foster City, Calif.). As shown in FIG. 7, the sequence determined shows a gene with a total of two exons interrupted by an 1800 bp intron. The deduced amino acid sequence (FIG. 9) of the complete open reading frame (FIG. 8) gives a protein of 387 amino acids with features typical of G protein-coupled receptors including 7 transmembrane alpha helical domains. FIG. 14 shows an alignment of GALR1 and GALR2 protein sequences with the seven transmembrane domains underlined. The human GALR2 protein bears strong sequence identity and similarity to the rat GALR2 ortholog. One notable difference between the human and rat forms is the presence of an additional 15 amino acids in the C-terminal intracellular domain of human GALR2.

EXAMPLE 7

Receptor Expression: Human and Rat GALR2: Construction of Human GalR2 Expression Plasmid The human GalR2 expression construct was assembled from the human genomic clone by PCR. Each exon was PCR amplified using standard conditions. The primers for exon I were: Forward, Exon I (5'-CCG GAA TTC GGT ACC ATG AAC GTC TCG GGC TGC CC-3'; SEQ ID NO:12) and Reverse, Exon I (5'-GGT AGC GGA TGG CCA GAT ACC TGT CTA GAG AGA CGG CGG CC-3'; SEQ ID NO:13). The primers for exon II were: Forward, Exon II (5'-GGC CGC CGT CTC TCT AGA CAG GTA TCT GGC CAT CCG CTA CC- 3'; SEQ ID NO:14) and Reverse, Exon II (5'-GGC CGC CGT CTC TCT AGA CAG GTA TCT GGC CAT CCG CTA CC-3'; SEQ ID NO:15). PCR products were subcloned in to pBluescript and sequenced. Exon I product was subcloned into the EcoRI and XbaI sites of plasmid pCINeo (Promega, Madison, Wis.). Exon II was then cloned into the XbaI site and the orientation determined by appropriate restriction digests and DNA sequencing.

EXAMPLE 8

Radioligand Binding Assay

Plasmid DNA was prepared using the Qiagen Maxi protocol (Qiagen, Chatsworth, Calif.) and transfected into COS-7 cells by electroporation. Briefly, 0.85 μl COS-7 cells in Ringers' buffer (1.2×10$^7$/ml) and 20 μg of DNA were mixed in a 0.4 mm electroporation cuvette (Bio-Rad, Hercules, Calif.) and current (960 μF, 260 V) was applied using a Bio-Rad Electroporator device. Cells were transferred to a T-180 flask (Corning) with fresh media and expression was allowed to proceed for 72 hrs. Membranes were prepared from transfected cells following disruption in enzyme-free dissociation solution (Specialty Media, Lavallette, N.J.) in a Dounce homogenizer in ice-cold membrane buffer (10 mM Tris, pH 7.4, 10 mM PMSF, 10 μM phosphoramidon, and 40 μg/ml bacitracin). After a low speed (1100×g, 10 min. at 4° C.) and a high speed centrifugation (38,700×g for 15 min. at 4° C.), membranes were suspended in buffer and the protein concentration determined (Bio-Rad assay kit). Binding of $^{125}$I-human galanin (sp. act=2200 Ci/mmol, DuPont NEN) was measured in membranes using a buffer of 25 mM Tris pH 7.4, 0.5% BSA, 2 mM $MgCl_2$, 40 μg/ml bacitracin, 4 μg/ml phosphoramidon, and 10 μM leupeptin in a total volume of 0.25 ml. 70 pm $^{125}$I-human galanin was used. Reactions were initiated by the addition of membranes and the incubation was allowed to proceed at room temperature for 1 hour. Non-specific binding was defined as the amount of membrane bound radioactivity remaining in the presence of 1 μM cold galanin. In competition studies various concentrations of peptides (hGal, pGal, hGal(1-16), rGAL(2-29), rGAL(3-29), hGal (1-19) or chimeric peptides (C7, M15, M40, M35) were included along with $^{125}$I-hGal (70 pmol). Incubations were terminated by rapid filtration through GF/C filters which had been presoaked with 0.1% polyethylamine using a TOMTEC (Orange, Conn.) cell harvester. The results were analyzed using the Prism software package (GraphPad, San Diego, Calif.).

Recombinant expression of human GALR2 binding sites in transiently transfected COS-7 permitted the determation of pharmacology of the cloned receptor. $^{125}$I-human galanin bound to the cloned GALR2 receptor with high affinity in a saturable and specific manner with a $K_D$ of 5 nM. As summarized in FIG. 10, competition of $^{125}$I-human galanin with a variety of galanin-derived peptides and chimeric peptide antagonist/partial agonists showed that the human GALR2 receptor has a similar pharmacology of binding to that of the rat GALR2.

EXAMPLE 9
Functional Characterization: Post-receptor Signalling Mechanism Frog Melanophore Assay Growth of *Xenopus laevis* melanophores and fibroblasts was performed as described previously (Potenza, M. N. et al, 1992, *Pigment Cell Res.* 3:38–43). Briefly, melanophores were grown in fibroblast-conditioned growth medium. The fibroblast-conditioned growth medium was prepared by growing fibroblasts in 70% L-15 medium (Sigma), pH 7.3, supplemented with 20% heat-inactivated fetal bovine serum (Gibco), 100 μg/ml streptomycin, 100 units/ml penicillin and 2 mM glutamine at 27.5° C. The medium from growing fibroblasts was collected, passed through a 0.2 μm filter (fibroblast-conditioned growth medium) and used to culture melanophores at 27.5° C.

Plasmid DNA was transiently transfected into melanophores by electroporation using a BTX ECM600 electroporator (Genetronics, Inc. San Diego, Calif.). Melanophores were incubated in the presence of fresh fibroblast-conditioned frog medium for 1 hour prior to harvesting of cells. Melanophore monolayers were detached by trypsinization (0.25% trypsin, JHR Biosciences), followed by inactivation of the trypsin with fibroblast-conditioned frog medium. The cells were collected by centrifugation at 200×g for 5 minutes at 4° C. Cells were washed once in fibroblast conditioned frog medium, centrifuged again and resuspended at 5×10$^6$ cells per ml in ice cold 70% PBS pH 7.0. 400 μl aliquots of cells in PBS were added to prechilled eppendorf tubes containing 2 μg of pcIneo:human Galanin 2 receptor plasmid DNA mixed with control receptor cDNA and naked vector DNA for a total of 20 μg DNA (2 μg each of pcDNA1amp:cannabinoid 2 and pcDNA3: thromboxane A2 receptor plasmid DNA, and 18 μg of pcDNA3.1 plasmid DNA in 40 μl total volume, or 2 μg each of pcDNA1amp:cannabinoid 2 and pcDNA3:thromboxane A2 receptor plasmid DNA, and 20 μg of pcDNA3.1 plasmid DNA in 40 μl total volume, as a control). Samples were incubated on ice for 20 min, and mixed every 7 minutes. Cell and DNA mixes were transferred to prechilled 2 mM gap electroporation cuvettes (BTX) and electroporated with the following settings: capacitance of 325 microfarad, voltage of 450 volts and resistance of 720 ohms. Immediately following electroporation, cells were mixed with fibroblast-conditioned frog medium (7.85 mls per cuvette) and plated onto flat bottom 96 well microtiter plates (NUNC). Electroporations from multiple cuvettes were pooled together prior to plating to ensure homogenous transfection efficiency. On the day following transfection, medium was removed and fresh fibroblast-conditioned frog medium was added to the melanophore monolayer and cell were incubated at 27° C.

Cells were assayed for receptor expression 2 days following transfection in 96-well plate format. On the day of ligand stimulation, medium was removed by aspiration and cells were washed with 70% L-15 containing 15 mM HEPES pH 7.3 (Sigma). Assays were dividing into two separate parts in order to examine Gs/Gq functional coupling which results in pigment dispersion in melanophores, or Gi functional coupling which results in pigment aggregation. For Gs/Gq functional coupling responses, assays were performed as follows. Cells were incubated in 100 μl of 70% L-15 containing 15 mM HEPES for 1 hour in the dark at room temperature, and then incubated in the presence of melatonin (2 nM final concentration) for 1 hour in the dark at room temperature to induce pigment aggregation. Initial absorbance at 600 nM was measured using a Bio-Tek Elx800 Microplate reader (ESBE Scientific) prior to addition of ligand. Human galanin (Peninsula) was added in duplicate wells, samples were mixed and incubated in the dark at room temperature for 1 hour, after which the final absorbance at 600 nm was determined. For Gi coupled responses, cell monolayers were incubated in the presence of 100 μl of 70% L-15 containing 2% fibroblast-conditioned growth medium, 2 mM glutamine, 100 ug/ml streptomycin, 100 units/ml penicillin and 15 mM HEPES for 15 minutes in the dark at room temperature to preset the cells to dispersion. After initial absorbance at 600 nM was determined, human galanin was added to cell monolayers, samples were mixed, incubated in the dark for 1.5 hour at room temperature and then final absorbances were determined. Absorbance readings were converted to transmission values in order to quantitate pigment dispersion using the following formula: 1−Tf/Ti, where Ti=the initial transmission at 600 nm and Tf=the final transmission at 600 nm. Pigment aggregation was quantitated using the following formula: Af/Ai−1, where Af=final absorbance at 600 nm and Ai is initial absorbance at 600 nm.

Figure 11A:
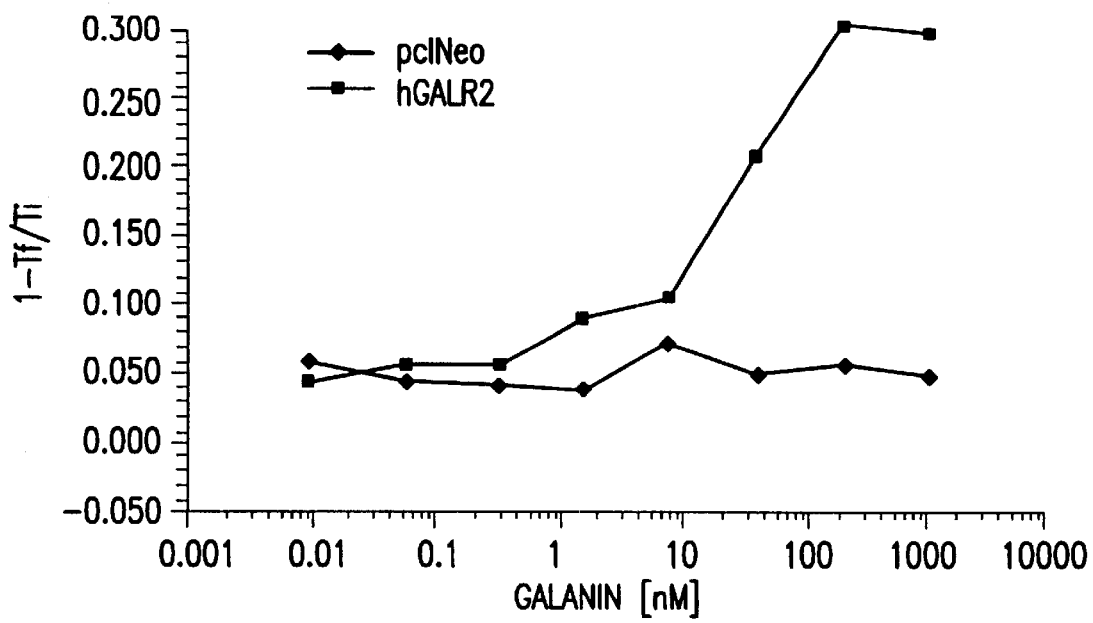
FIG. 11 illustrates $G_q$ or $G_s$ coupled response (pigment dispersion) as well as $G_i$-coupled response (pigment aggregation).
Figure 11B:
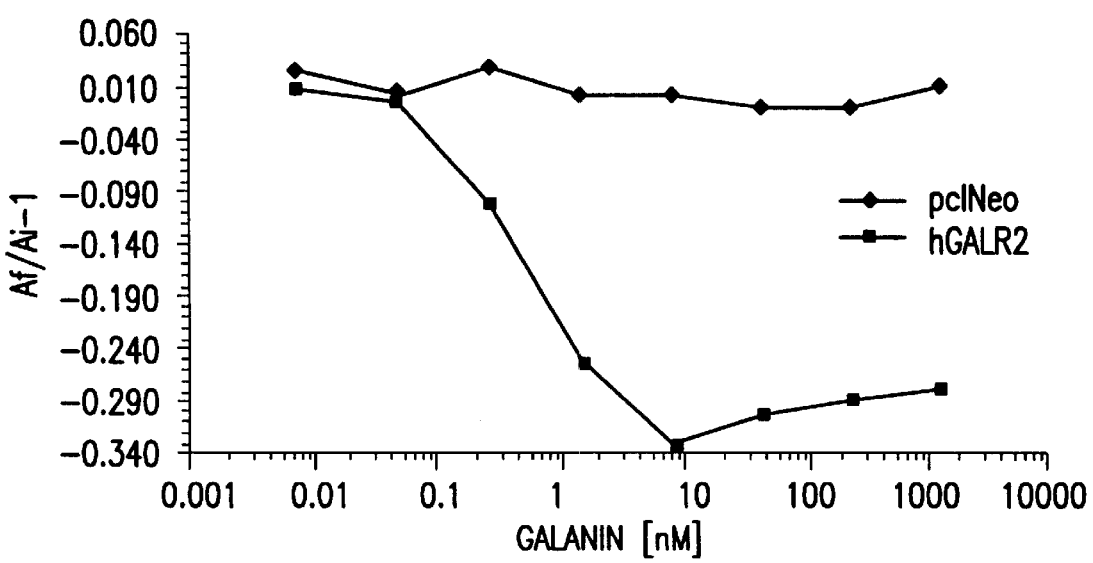

To determine whether the human GALR2 could be functionally expressed in melanophores, the expression plasmid pcIneo:hGALR2 was transiently transfected by electroporation into melanophores followed by stimulation of the transfected cells with human galanin. Increasing doses of galanin resulted in a dose-dependent dispersion of pigment in human GALR2-transfected melanophores, in contrast to control vector-transfected cells (FIG. 11). The apparent $EC_{50}$ for human galanin in pcIneo:hGALR2-transfected melanophores was 20 nM, in general agreement with specific $^{125}$human galanin binding in pcIneo:hGALR2-transfected COS-7 cells ($IC_{50}$~4 nM). The dispersion of pigment in the melanophore has been previously shown to occur either through Gαs coupling and stimulation of adenylyl cyclase or through Gαq coupling and mobilization of calcium.

There was no detectable aggregation of the pigment in either the pcIneo:hGALR2- or mock-transfected melanophores following incubation in the presence of 0.001–1000 nM human galanin. This result suggests that the hGALR2 does not couple to Gαi-mediated signaling pathways.

EXAMPLE 10

Aequorin Bioluminescence Assay

Measurement of GALR2 expression in the aequorin-expressing stable reporter cell line 293-AEQ17 (Button, D et al, 1993 "Aequorin-expressing mammalian cell lines used to report $Ca^{2+}$ mobilization" *Cell Calcium* 14:663–671) was performed using a Luminoskan RT luminometer (Labsystems Inc., Gaithersburg, Md.) controlled by custom software written for a Macintosh PowerPC 6100. 293-AEQ17 cells ($8 \times 10^5$ cells plated 18 hrs. before transfection in a T75 flask) were transfected with 22 µg of rat or human GALR2 plasmid DNA: 264 µg lipofectamine. Following approximately 40 hours of expression the apo-aequorin in the cells was charged for 4 hours with coelenterazine (10 µM) under reducing conditions (300 µM reduced glutathione) in ECB buffer (140 mM NaCl, 20 mM KCl, 20 mM HEPES-NaOH [pH=7.4], 5 mM glucose, 1 mM $MgCl_2$, 1 mM $CaCl_2$, 0.1 mg/ml bovine serum albumin). The cells were harvested, washed once in ECB medium and resuspended to 500,000 cells/ml. 100 µl of cell suspension (corresponding to $5 \times 10^4$ cells) was then injected into the test plate, and the integrated light emission was recorded over 30 seconds, in 0.5 second units. 20 mL of lysis buffer (0.1% final Triton X-100 concentration) was then injected and the integrated light emission recorded over 10 seconds, in 0.5 second units. The "fractional response" values for each well were calculated by taking the ratio of the integrated response to the initial challenge to the total integrated luminescence including the Triton-X100 lysis response.

The aequorin bioluminescence assay is a reliable test for identifying G protein-coupled receptors which couple through the Ga protein subunit family consisting of Gq and G11 which leads to the activation of phospholipase C, mobilization of intracellular calcium and activation of protein kinase C. Based on the above melanophore data for GALR2, utilization of the aequorin bioluminescence assay permitted the discrimination between the two possibilities for the primary intracellular signaling mechanism for GALR2, namely Gαs coupling and stimulation of adenylyl cyclase or Gαq coupling and mobilization of calcium. Expression of human or rat GALR2 in the aequorin-expressing 293 cell line (293-AEQ17) gave a dose-dependant increase in aequorin bioluminescence in response to challenge by galanin and several related peptides. Transfection of human GALR1, which signals through Gi and the inhibition of adenylyl cyclase, gave no galanin-dependant increase in aequorin bioluminescence. Responses observed for human or rat GALR2 activation were saturable and the rank order of potency was similar to that observed for competition studies for $^{125}$-human galanin binding. $EC_{50}$'s, given in nM for the human GALR2 (results were similar for the rat GALR2 ortholog) were: human galanin, 32; rat galanin, 12; rat galanin (2-29), 31; rat galanin (3-29)>10, 000; M35, 44; M40, 8.8. Of interest to note is that the galanin chimeric peptide antagonists (M35 and M40), thought by some to be pure antagonists on the GALR1 receptor, appear to be partial agonists on the GALR2 receptor. These data indicate that the primary signaling mechanism for GALR2 is through the phopholipase C/protein kinase C pathway, in contrast to GALR1, which communicates its intracellular signal by inhibition of adenylyl cyclase through Gi. In addition, while binding and activation of the rat and human GALR2 receptor by galanin is of high affinity and potency, rat or human GALR1 binds and is activated by galanin at a 10–30 fold lower concentration. This observation points to the existence of other undiscovered naturally-occurring ligand systems that may be agonists at the GALR2 receptor.

EXAMPLE 11

RNA Expression Profile of Human GalR2

Northern blotting analysis was utilized to assess the tissue specificity of human GALR2 mRNA expression. As shown in FIG. 15, modest expression (indicated by one "+") is seen in a variey of brain regions and peripheral tissues, as observed for the rat ortholog of GALR2. The most prevalent transcript size is ~2.2 kb with a band of ~1.5 kb observed in spleen, thymus and prostate. Tissues with significantly higher expression levels (indicated by two or three "+") were placenta, thymus and prostate.

EXAMPLE 12

Chromosome Localization of Human GalR2 Gene

Fluorescence in situ hybridization (FISH) of metaphase spread chromosomes derived from human lymphocytes together with DAPI banding patterns was used to map hGalR2 to its chromosome, as described (Heng, H. H. Q. and Tsui, L.-C. *Modes of DAPI banding and simultaneous in situ hybridization.* Chromosoma 102:325–332). FISH data localize the receptor gene to human chromosome 17q25.

EXAMPLE 13

Mouse GALR2: Clone Isolation: Cloning of Mouse GalR2 Genomic Clone

DNA fragments from the Human GalR2 gene were radio-labelled with [32P]dCTP by random octomer labeling (Gibco BRL) and used as a probe to screen a mouse 129sv genomic library (Stratagene). Positive phage clones were plaque purified, DNA was prepared, restriction enzyme digested, electrophoresed on an agarose gel, transferred to nylon membrane, and hybridized with the same probe used to screen the library. A positive NotI fragment was subcloned into pBluescript (Stratagene).

EXAMPLE 14

Gene Sequence and Structure

DNA sequence encoding the complete ORF for mouse GALR2 (SEQ ID NO:12) is shown in FIG. 12. A single intron of 1060 bp divides the ORF into two exons. Removal of the intron allows for conceptual translation to give the predicted GALR2 polypeptide of 371 amino acids (SEQ ID NO:13) as shown in FIG. 13. Compared to both the human and rat orthologs, the mouse protein sequence bears strong identity (85% and 96% respectively).

What is claimed:

1. An isolated nucleic acid encoding rat galanin receptor (GALR2), substantially free from associated nucleic acids, comprising a nucleotide sequence encoding for the amino acid sequence of SEQ ID NO: 20.

2. The nucleic acid of claim 1, wherein said nucleotide sequence is SEQ D NO: 19.

3. A vector comprising a nucleotide sequence encoding for the amino acid sequence of SEQ ID NO: 20.

4. The vector of claim 3, wherein said nucleotide sequence is SEQ ID NO: 19.

5. A host cell comprising the vector of claim 3.

6. A cell comprising the vector of claim 4.

* * * * *